United States Patent
Tanaka et al.

(10) Patent No.: US 7,031,872 B2
(45) Date of Patent: Apr. 18, 2006

(54) EQUILIBRIUM STATE ANALYZING APPARATUS, EQUILBRIUM STATE ANALYSIS METHOD, PROGRAM AND RECORDING MEDIUM

(75) Inventors: Shinji Tanaka, Osaka (JP); Shigeyuki Inoue, Kyoto (JP); Hirosi Yamamoto, Osaka (JP); Sachio Nagamitsu, Kyoto (JP); Yoshitaka Kawasaki, Mie (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 4 days.

(21) Appl. No.: 10/497,327

(22) PCT Filed: Aug. 8, 2003

(86) PCT No.: PCT/JP03/10108

§ 371 (c)(1),
(2), (4) Date: Jun. 1, 2004

(87) PCT Pub. No.: WO2004/014230

PCT Pub. Date: Feb. 19, 2004

(65) Prior Publication Data

US 2005/0021312 A1 Jan. 27, 2005

(30) Foreign Application Priority Data

Aug. 9, 2002 (JP) ............................. 2002-232221
Aug. 9, 2002 (JP) ............................. 2002-232222

(51) Int. Cl.
*G06F 11/32* (2006.01)
(52) U.S. Cl. ...................................... 702/141; 324/160
(58) Field of Classification Search ................ 702/141, 702/150; 324/160, 178
See application file for complete search history.

(56) References Cited

U.S. PATENT DOCUMENTS

| | | | |
|---|---|---|---|
| 6,160,478 A | 12/2000 | Jacobsen et al. | |
| 6,546,291 B1* | 4/2003 | Merfeld et al. | 607/62 |
| 2004/0097839 A1* | 5/2004 | Epley | 600/595 |

FOREIGN PATENT DOCUMENTS

| | | |
|---|---|---|
| JP | 2760472 | 3/1998 |
| JP | 10-111990 | 4/1998 |
| JP | 10-165395 A | 6/1998 |
| JP | 2823841 | 9/1998 |
| JP | 2823842 | 9/1998 |
| JP | 2000-166877 A | 6/2000 |
| JP | 2000-193520 A | 7/2000 |
| JP | 2002-056483 | 2/2002 |
| JP | 2003-220039 A | 8/2003 |

OTHER PUBLICATIONS

Japanese International Search Report for PCT/JP03/10108, dated Oct. 14, 2003.

* cited by examiner

*Primary Examiner*—Edward Raymond
(74) *Attorney, Agent, or Firm*—RatnerPrestia

(57) ABSTRACT

An equilibrium state analyzing apparatus, equilibrium state analysis method, program thereof and recording medium are provided that place few constraints on the degree of freedom in the area of motion or posture of the examinee. An equilibrium state analyzing apparatus includes acceleration information detector, attached to the trunk of the human body, of detecting accelerations generated in at least one direction within the horizontal plane, motion information storing device of storing the detected accelerations, and equilibrium state analyzer of analyzing the equilibrium state of the human body using the stored acceleration information.

17 Claims, 24 Drawing Sheets

● : G; CENTER OF GRAVITY PROJECTED ONTO HORIZONTAL PLANE
Ax: ACCELERATION IN RIGHTWARD/LEFTWARD DIRECTION
Ay: ACCELERATION IN FRONTWARD/BACKWARD DIRECTION
$V_T$: FLUCTUATING VELOCITY

● : G; CENTER OF GRAVITY PROJECTED ONTO HORIZONTAL PLANE
Ax: ACCELERATION IN RIGHTWARD/LEFTWARD DIRECTION
Ay: ACCELERATION IN FRONTWARD/BACKWARD DIRECTION
$V_T$: FLUCTUATING VELOCITY

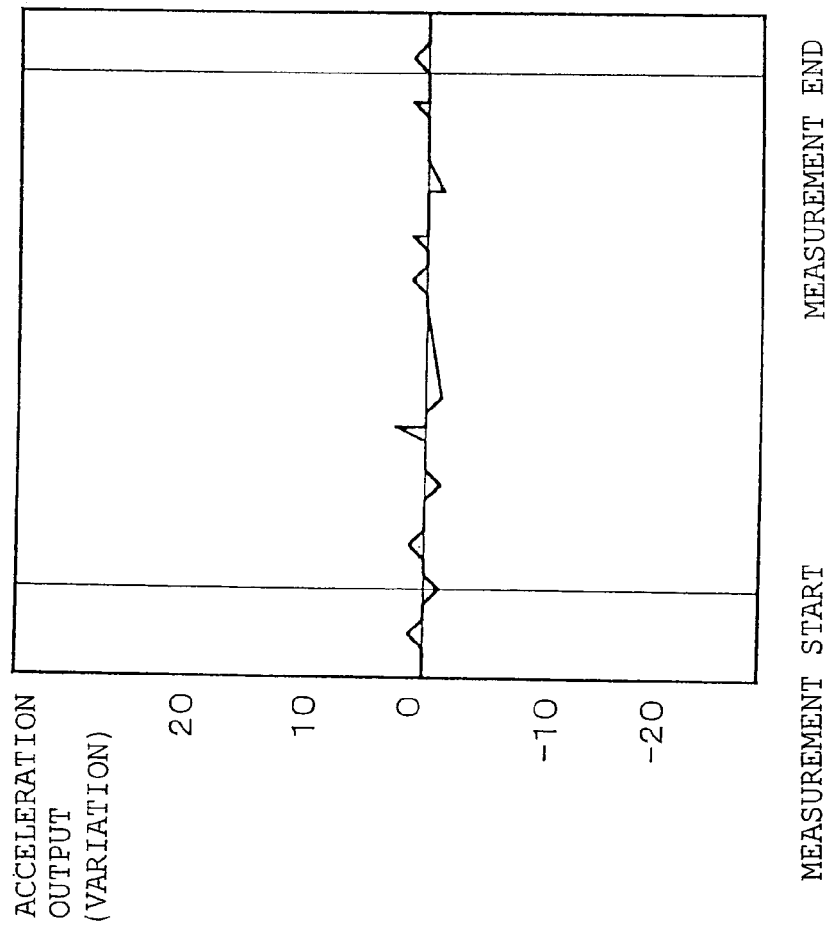

$$St = 1/2 \cdot t2 \cdot (Ax2 + Ay2)^{\wedge}1/2$$

EQUILIBRIUM STATE ANALYZING APPARATUS, EQUILBRIUM STATE ANALYSIS METHOD, PROGRAM AND RECORDING MEDIUM

This application is a U.S. National Phase Application of PCT International Application PCT/JP03/10108.

TECHNICAL FIELD

The present invention relates to an equilibrium state analyzing apparatus, equilibrium state analysis method, program thereof and recording medium applicable to an apparatus of inspecting physical functioning such as a center of gravity fluctuation meter, self-support of people including aged people, equipment, service or residence facilities, etc. for supporting rehabilitation.

BACKGROUND ART

With a background of the oncoming of an aging society, care-giving for aged people is becoming a focus of attention in recent years. Accidents caused by falling are seen as a problem particularly for aged people whose physical functions are debilitated. Furthermore, the role of rehabilitation is believed to increase drastically in the future from the standpoint of returning for aged people into society. Moreover, the consciousness of health care is growing among not only aged people but also ordinary citizens in general in recent years.

In such a background, preventing falling and establishing indices for health care or indices that allow objective judgment of the progress of rehabilitation are believed to grow in importance considerably in the future.

Conventionally, outputs from an acceleration sensor or inclination sensor are proposed as the methods of detecting falling. Furthermore, with respect to rehabilitation, a doctor or helper accompanies the patient and watches him/her all the time and judgment on the progress of rehabilitation is left up to the doctor or helper.

Furthermore, since the possibility of falling generally increases as fluctuation of the center of gravity intensifies, a technique of measuring the degree of fluctuation of the center of gravity is used as a measure of danger of falling and is also being gradually introduced at medical work fronts as an apparatus of detecting fluctuation of the center of gravity. This apparatus is also used to measure the progress of rehabilitation by observing variations in fluctuation of the center of gravity on a time-series basis. As this apparatus of detecting fluctuation of the center of gravity, an apparatus that records fluctuation of the center of gravity with an examinee mounting on a pressure detection plate (floor reaction force meter), etc., already exists (e.g., see Japanese Patent No. 2760472, Japanese Patent No. 2823841 and Japanese Patent No. 2823842, the entire disclosure of which are incorporated herein by reference in its entirety).

As described above, introduction of some apparatuses is being started as the apparatus of detecting fluctuation of the center of gravity from the standpoints of prevention of falling and rehabilitation, but the prices of those apparatuses are expensive, as they can cost several thousands of dollars. For this reason, though the importance of the apparatuses is widely recognized, they have not become widespread in general hospitals and are merely owned by those medical doctors specializing in neurological internal medicine, etc., who are interested in data itself of the apparatuses of detecting fluctuation of the center of gravity.

Furthermore, since the conventional apparatuses are of a stationary type, they require dedicated installation places and take time and effort in measurement and cannot be said to be easy to use.

Furthermore, for an analysis of an equilibrium state according to these prior arts, the examinee must mount on a load detecting means such as a pressure detection plate and the problem is that the area in which motion takes place or posture is limited to an extremely narrow area.

DISCLOSURE OF THE INVENTION

The present invention has been implemented in view of the above described problems and it is an object of the present invention to provide an equilibrium state analyzing apparatus, equilibrium state analysis method, program thereof and recording medium by placing fewer constraints on the degree of freedom in the area of motion or posture of the examinee.

A first aspect of the present invention is an equilibrium state analyzing apparatus comprising:

acceleration information detecting means, attached to the trunk of the human body, of detecting accelerations generated in at least one direction within the horizontal plane;

motion information storing means of storing said detected accelerations; and equilibrium state analyzing means of analyzing the equilibrium state of the human body by integrating said stored acceleration information.

A second aspect of the present invention is the equilibrium state analyzing apparatus according to the first aspect of the present invention, wherein said acceleration information detecting means can detect accelerations generated in the x- and y-directions which cross each other at right angles within the horizontal plane, and said equilibrium state analyzing means calculates and outputs velocities by integrating acceleration generated in said x-direction and acceleration generated in said y-direction, respectively.

A third aspect of the present invention is the equilibrium state analyzing apparatus according to the second aspect of the present invention, wherein said velocity ($V_t$) is calculated from:

$$V_t = \sqrt{\left(\int_{t-1}^{t} Ax t\, dt\right)^2 + \left(\int_{t-1}^{t} Ay t\, dt\right)^2} \quad \text{(Formula 1)}$$

$$\overline{V} = \text{Average}(Vt) \quad (t = 0, 1, 2, \ldots T)$$

where $Ax_t$ is the acceleration in said x-direction, $Ay_t$ is the acceleration in said y-direction (t is a sampling timing, t=0, 1, 2 . . . P/I, P is a measuring time and I is a sampling interval) and said equilibrium state analyzing means calculates and outputs an average velocity over the measuring time P from said calculated velocity ($V_t$).

A fourth aspect of the present invention is the equilibrium state analyzing apparatus according to the third aspect of the present invention, further comprising a display device of displaying said output data, wherein said motion information storing means stores said calculated average velocity and said measured date data, and said equilibrium state analyzing means displays said calculated average velocity corresponding to said date data stored in said motion information storing means on said display device over time.

A fifth aspect of the present invention is the equilibrium state analyzing apparatus according to the second aspect of the present invention, further comprising individual information setting means of setting individual-specific IDs and information controlling means of controlling the output from the equilibrium state analyzing means corresponding to each ID, characterized in that the output from the equilibrium state analyzing means corresponding to each ID is provided as an index.

A sixth aspect of the present invention is the equilibrium state analyzing apparatus according to the first aspect of the present invention, characterized in that the equilibrium state analyzing means totalizes and outputs the stored acceleration information corresponding to the time from the start to end of the measurement of acceleration.

A seventh aspect of the present invention is the equilibrium state analyzing apparatus according to the sixth aspect of the present invention, further comprising a display device of displaying the output data, characterized in that the motion information storing means stores the totalized acceleration and the measured date data and the equilibrium state analyzing means outputs the totalized acceleration corresponding to the date data stored in the motion information storing means to the displaying means over time.

An eighth aspect of the present invention is the equilibrium state analyzing apparatus according to the sixth aspect of the present invention, characterized in that the equilibrium state analyzing means ranks the totalized acceleration information.

A ninth aspect of the present invention is the equilibrium state analyzing apparatus according to the first aspect of the present invention, characterized in that the acceleration information detecting means can detect accelerations generated in the x- and y-directions which cross each other at right angles within the horizontal plane, the equilibrium state analyzing means calculates and outputs displacement in the center of gravity of the human body by integrating the acceleration generated in the x-direction and the acceleration generated in the y-direction twice respectively.

A tenth aspect of the present invention is the equilibrium state analyzing apparatus according to the ninth aspect of the present invention, characterized in that the displacement ($S_t$) and the center of gravity fluctuation index ($G_n$) (n: measuring count) are calculated from:

$$S_t = 1/2 \times t^2 \times (Ax^2 + Ay^2)^{1/2} \quad \text{(Formula 2)}$$

$$G_n = \int_0^T S_t \, dt$$

where Axt is the acceleration in the x-direction, Ayt is the acceleration in the y-direction (t is a sampling timing, t=0, 1, 2 . . . P/I, P is a measuring time and I is a sampling interval), and the equilibrium state analyzing means outputs the calculated displacement and the center of gravity fluctuation index.

An eleventh aspect of the present invention is the equilibrium state analyzing apparatus according to the tenth aspect of the present invention, characterized in that the equilibrium state analyzing means compares the calculated $G_n$ with $G_1, G_2, \ldots G_{n-1}$ and outputs "good" when $G_n < G_{n-1}$ and outputs "fair" when $G_n = G_{n-1}$ and outputs "caution" when $G_n > G_{n-1}$.

A twelfth aspect of the present invention is the equilibrium state analyzing apparatus according to the tenth aspect of the present invention, characterized in that the equilibrium state analyzing means decides that the body is in a stationary standing position when the displacement is within a predetermined area from the position of the center of gravity of the human body and decides that the human body is falling or in a transition toward falling when the displacement is outside the predetermined area.

A thirteenth aspect of the present invention is the equilibrium state analyzing apparatus according to the first aspect of the present invention, further comprising standing position signal inputting means, connected to the equilibrium state analyzing means, of inputting a standing position signal, characterized in that the equilibrium state analyzing means starts an analysis of the equilibrium state when the standing position signal is input to the standing position signal inputting means.

A fourteenth aspect of the present invention is an equilibrium state analysis method comprising an acceleration information detecting step of detecting acceleration generated in at least one direction within the horizontal plane by acceleration information detecting means mounted in the trunk of the body, a motion information storing step of storing the detected acceleration and an equilibrium state analyzing step of analyzing the equilibrium state of the human body by integrating the stored acceleration information.

A fifteenth aspect of the present invention is a program for operating a computer as the motion information storing means of storing the detected acceleration and the equilibrium state analyzing means of analyzing the equilibrium state of the human body by integrating the stored acceleration information in the equilibrium state analyzing apparatus according to the first aspect of the present invention.

A sixteenth aspect of the present invention is a recording medium which stores the program according to the fifteenth aspect of the present invention and which can be processed by a computer.

The present invention can provide an equilibrium state analyzing apparatus, equilibrium state analysis method, program thereof and recording medium which place fewer constraints on the degree of freedom in the area of motion and posture of an examinee.

BRIEF DESCRIPTION OF DRAWINGS

FIGS. 14(a) and 14(b) are schematic diagrams of a template example of the equilibrium state analyzing apparatus according to Embodiment 4 of the present invention;

DESCRIPTION OF SYMBOLS

Figure 1:
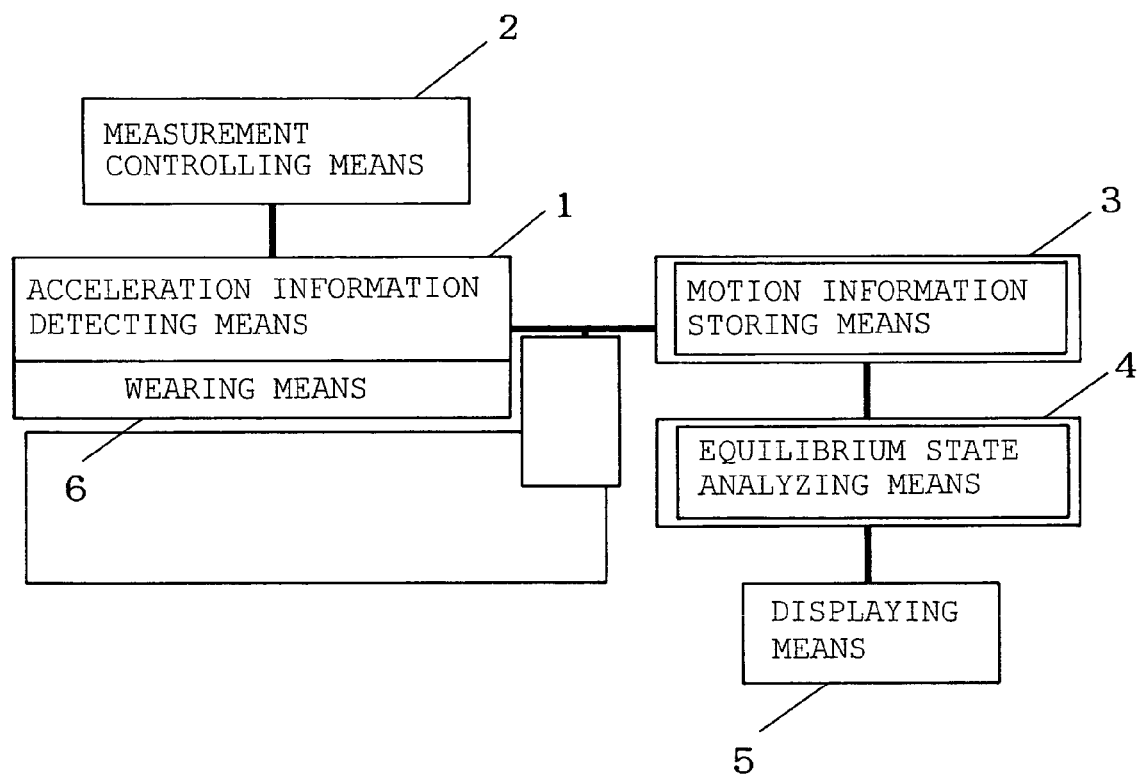
FIG. 1 is a block diagram of an equilibrium state analyzing apparatus according to Embodiment 1 of the present invention.

1 Acceleration information detecting means
2 Measurement controlling means
3 Motion information storing means
4 Equilibrium state analyzing means
5 Displaying means
6, 20 Wearing means
7 Standing position signal inputting means
8 Computer
9 Individual information setting means
10 Information controlling means
11 Control information presenting means
12 Host computer
19 Human body
22 Arrow indicating frontward orientation of human body
23 Arrow indicating rightward orientation of human body
s1 Measuring time setting step
s2 Acceleration information inputting step
s3 Equilibrium state analyzing step
s4 Motion information storing step
s5 Physical body information inputting step
s6 Physical body information deciding step
s7 Outputting step
111 Equilibrium state detection apparatus
122 Acceleration sensor
113 Signal processing means
114 Collection ROM
115 Calculating means
116 ROM
117 Displaying means
118 Holding member
121 Switch
131 Acceleration collection result
141 Storing means
151 Information transmitting means
152 Information receiving means
161 Cellular phone
162 User
201, 211, 216 Acceleration detection section
202 Communication control section
203 Motion analysis section
204 Information presentation section
205 Information control section Best Mode for Carrying Out the Invention With reference now to the attached drawings, embodiments of the present invention will be explained below.

Embodiment 1

Even when a person apparently stands still, the human body is keeping the standing position while it is always fluctuating. This fluctuation is fluctuation of the center of gravity and an index indicating the degree of the fluctuation is a center of gravity fluctuation index. The center of gravity fluctuation index is used to measure the motor functions such as human postural reflex and standing position keeping function, etc., and used to evaluate the location and degree of a dysfunction such as vertigo and equilibrium dysfunction. FIG. 1 is a block diagram of an equilibrium state analyzing apparatus according to Embodiment 1 of the present invention. Reference numeral 1 denotes acceleration information detecting means, 2 denotes measurement controlling means, 3 denotes motion information storing means, 4 denotes equilibrium state analyzing means, 5 denotes displaying means and 6 denotes wearing means.

Figure 2:
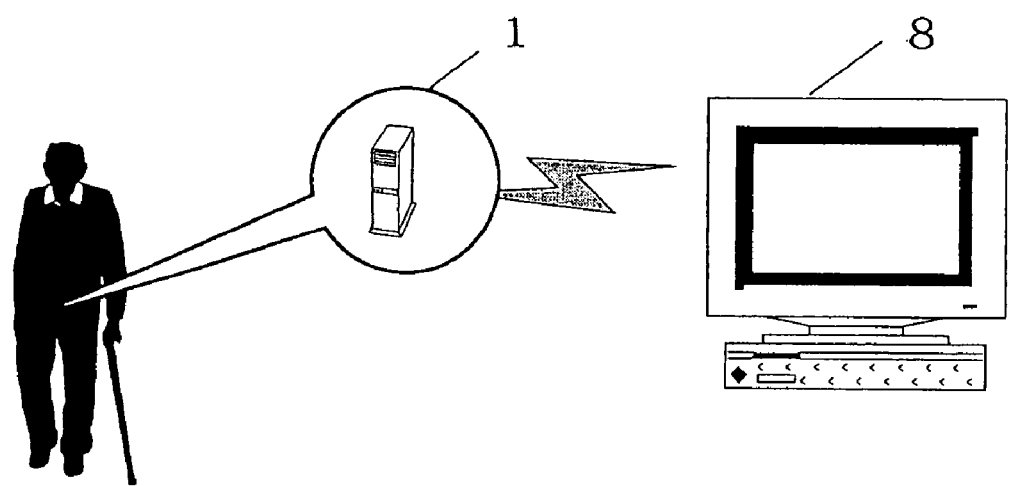
FIG. 2 is a schematic diagram of the equilibrium state analyzing apparatus according to Embodiment 1 of the present invention.
Figure 3:
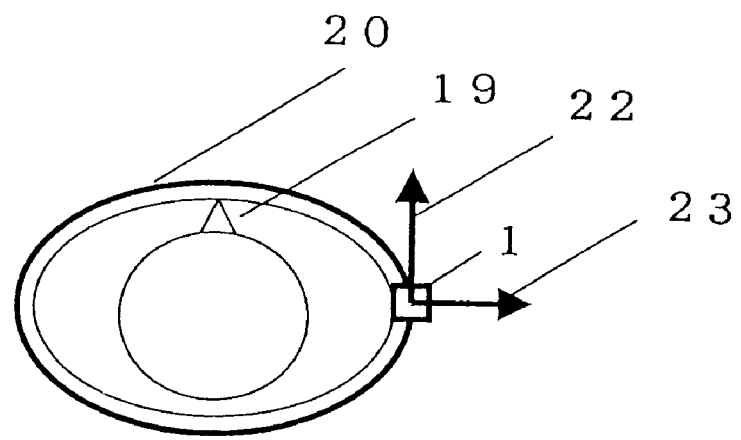
FIG. 3 is a top view illustrating an example of attaching the acceleration information detecting means according to Embodiment 1 of the present invention.

In this embodiment, as shown in FIG. 2, the acceleration information detecting means is fixed to the waist of the human body, that is, close to the right iliac crest through the wearing means 6. The measurement controlling means 2, equilibrium state analyzing means 4, motion information storing means 3 and displaying means 5 operate on a system based on a personal computer 8. The acceleration detection direction when the acceleration information detecting means 1 is attached close to the right iliac crest of the human body is shown in FIG. 3. FIG. 3 is a bird's eye view of the human body, reference numeral 19 in the figure denotes a human body, 20 denotes a belt-shaped wearing device wound around the human body, and 22 denotes the frontward/backward direction (frontward is assumed to be a positive direction) and 23 denotes the rightward/leftward (rightward is assumed to be a positive direction). According to this embodiment, in order to detect accelerations generated on the horizontal plane, the x-axis and y-axis which cross each other at right angles on the horizontal plane are assumed to be the frontward/backward direction and rightward/leftward direction of the human body, a two-axis acceleration sensor is provided as the acceleration information detecting means 1 so as to be able to detect accelerations in the respective directions. This arrangement allows the acceleration information detecting means 1 to detect accelerations generated on the horizontal plane caused by movement of the body as voltage values, A/D-convert and output them as digital values.

At this time, the measurement controlling means 2 sets sampling intervals for A/D conversion and switches the start/end of the operation of the acceleration information detecting means 1. Therefore, the acceleration information detecting means 1 outputs accelerations generated within the horizontal plane from the start to end of measurement at the set sampling intervals as digital values. Furthermore, the acceleration information detecting means 1 outputs calendar information having the date and time on which acceleration information is detected together with the acceleration information to the motion information storing means 3.

The equilibrium state analyzing means 4 inputs acceleration data from the motion information storing means 3 on a time-series basis, calculates a center of gravity fluctuation index and outputs it to the motion information storing means 3 and/or displaying means 5. The motion information storing means 3 stores not only the measured acceleration information but also the center of gravity fluctuation index. The displaying means 5 presents the center of gravity fluctuation index output from the equilibrium state analyzing means 4 together with calendar information which is ancillary information. These components allow one individual to perform a series of operations from analyzing an equilibrium state of the examinee to presentation of the result.

Figure 4:
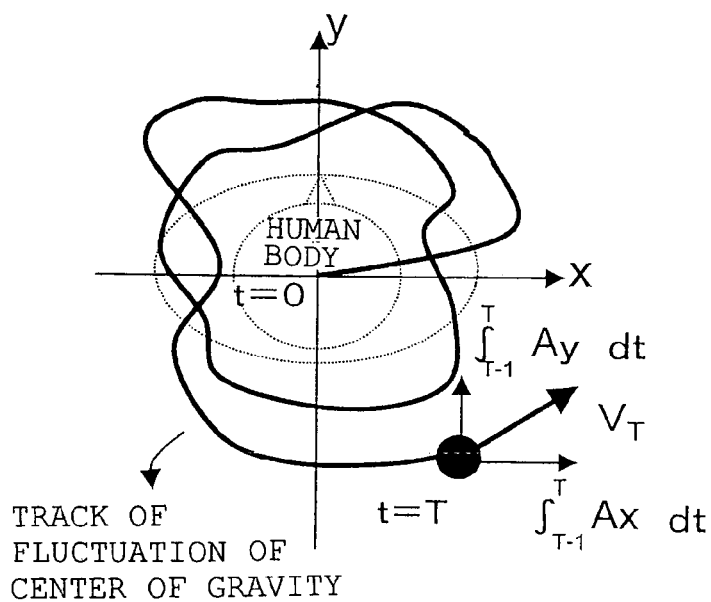
FIG. 4 is a schematic diagram of a center of gravity fluctuation index in the equilibrium state analyzing apparatus according to Embodiment 1 of the present invention.

FIG. 4 shows a schematic diagram of a center of gravity fluctuation index output from the equilibrium state analyzing means 1. In FIG. 4, suppose G is a projection of the center of gravity of the human body onto the horizontal plane, t is an elapsed time and VT is an fluctuation velocity indicating the track of G after measurement start time T has elapsed and a velocity variation of movement of the center of gravity at T. In this case, the center of gravity fluctuation index at T is defined by a section average of an elapsed time (from t=0 to t=T) of VT. Generally, when the center of gravity fluctuation increases, the length of the track shown in FIG. 4 increases. People make adjustments by subtly changing the moving direction of the center of gravity through muscles activities so that the center of gravity does not deviate from the stable basal surface made up of soles. However, when the center of gravity fluctuates, acceleration is generated by muscle activities, the magnitude and orientation of the velocity of movement of the center of gravity are changed, producing a track of the center of gravity for a certain time. The center of gravity fluctuation index in this embodiment is expressed using the magnitude of a velocity variation, VT, at this time.

Figure 5:
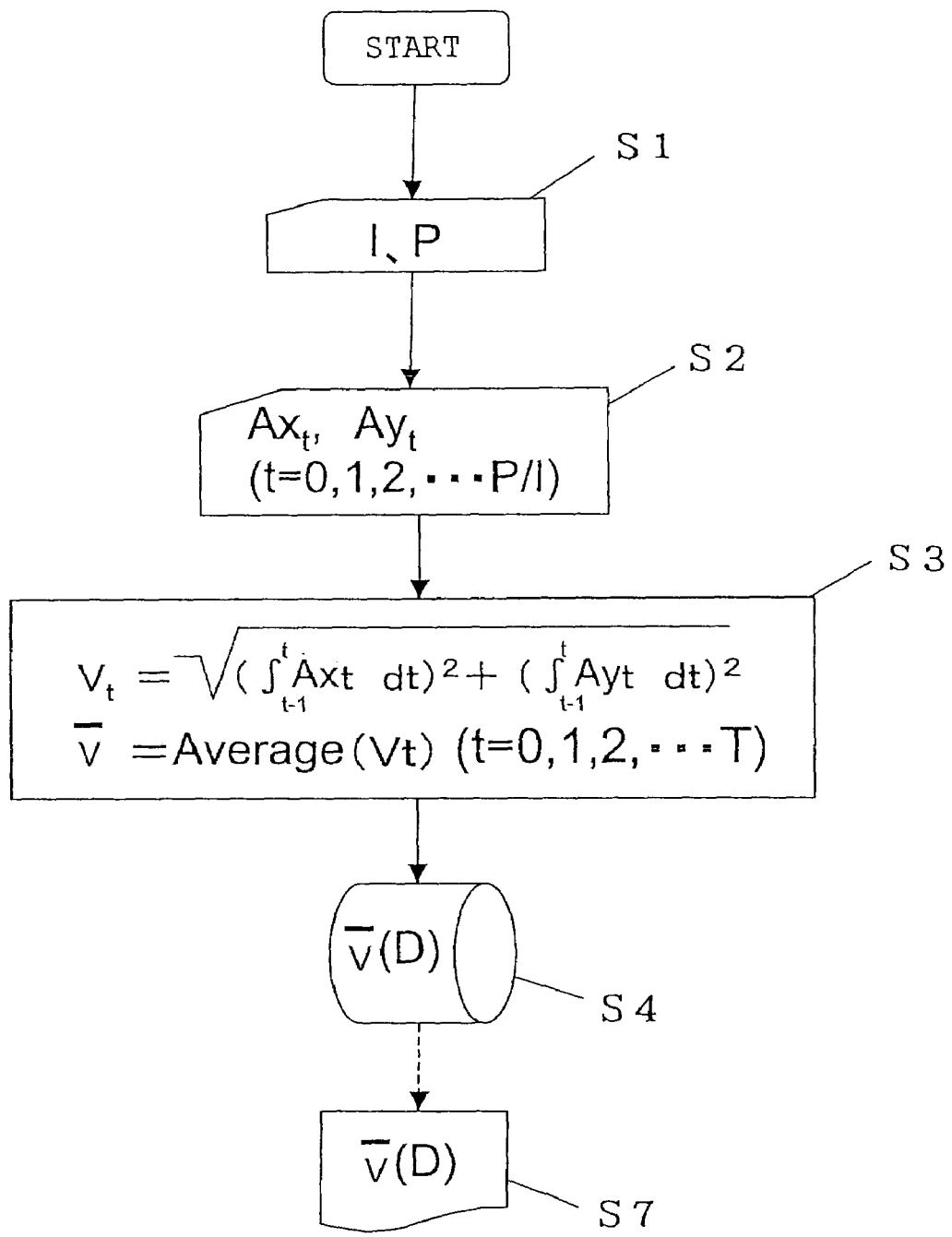
FIG. 5 is a flow chart showing an operation of the equilibrium state analyzing apparatus according to Embodiment 1 of the present invention.

A specific analysis algorithm of specific center of gravity fluctuation of the center of gravity fluctuation analyzing apparatus of Embodiment 1 is shown in FIG. 5. s1 denotes a measuring time setting step, s2 denotes an acceleration information inputting step, s3 denotes a center of gravity fluctuation analyzing step, s4 denotes a motion information storing step and s7 denotes an outputting step. When the algorithm starts, in the measuring time setting step s1, sampling interval I and measuring time setting step P are input. When the measuring time at this time is P and the sampling interval is I, the input count of acceleration information on two axes $Ax_t$ and $Ay_t$ is P/I. In the acceleration information inputting step s2, acceleration information of the two axes $Ax_t$ and $Ay_t$ are input and the unit of acceleration is added based on a calibration. In the calibration, the output value corresponding to 0G from the acceleration information detecting means 1 and the output value corresponding to 1G are stored in the equilibrium state analyzing means 4 and $Ax_t$ and $Ay_t$ are converted to accelerations. In this embodiment, it is assumed by way of example that the sampling interval (I) is 1 sec and measuring time (P) is 30 sec.

Then, as shown in (Formula 1), by integrating $Ax_t$ and $Ay_t$ for one sec in the center of gravity fluctuation analyzing step s3 and calculating the square root of the sum of the respective squares, a velocity per second Vt is calculated with respect to inputs of acceleration information on two axes $Ax_t$ and $Ay_t$. Then, a time average in a section of P sec with respect to Vt is calculated and the center of gravity fluctuation index is defined by this value. In integrating $Ax_t$ and $Ay_t$ above, an initial condition of Vt=0 when t=0 (that is, the examinee is in a standing position and stationary at the start of measurement) is used.

$$V_t = \sqrt{\left(\int_{t-1}^{t} Axt\, dt\right)^2 + \left(\int_{t-1}^{t} Ayt\, dt\right)^2} \qquad \text{(Formula 1)}$$

$$\overline{V} = \text{Average}(Vt) \qquad (t = 0, 1, 2, \dots T)$$

Then, when the above described operation is repeated, a plurality of center of gravity fluctuation indices are stored and it is possible to control the stored plurality of center of gravity fluctuation indices. For example, it is possible to attach calendar information to the center of gravity fluctuation indices and output the stored plurality of center of gravity fluctuation indices as time series information.

In the case of this embodiment, P=30 and I=1 are assumed, and therefore the input count of acceleration information $Ax_t$ and $Ay_t$ becomes 30, which is equal to P. According to this embodiment, in the measuring time setting step s1, the sampling interval I is set to 1 sec and the measuring time is set to P=30 sec and the operation is started when the examinee is in a standing position. When the operation starts, in the acceleration information inputting step s2, acceleration information on two axes $Ax_t$ and $Ay_t$ is input for 30 sec and the unit of acceleration is added based on the calibration. Since the measuring time P is 30 and the sampling interval I is 1 at this time, the input count of the acceleration information on two axes $Ax_t$ and $Ay_t$ becomes 30, which is equal to P. Then, in the center of gravity fluctuation analysis step s3, by integrating $Ax_t$ and $Ay_t$ for 1 sec and calculating the square root of the sum of their respective squares, the velocity per second Vt is calculated with respect to the inputs of the acceleration information on two axes $Ax_t$ and $Ay_t$. Then, the time average over a section of 30 sec is calculated to Vt and the center of gravity fluctuation index is defined by this value. Then, calendar information is attached to the center of gravity fluctuation analysis index and output as time series information V(D). In this embodiment, an integer is assigned to the suffix D of the array according to, for example, the order of dates on which input acceleration information is recorded.

Figure 6:
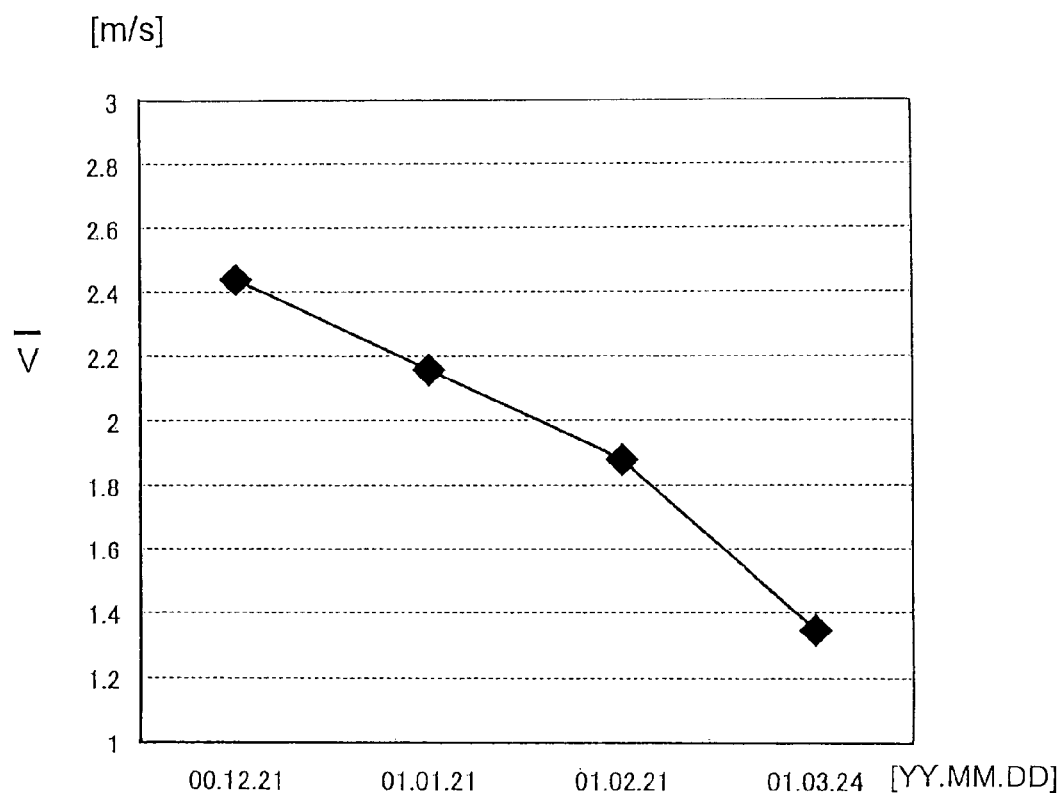
FIG. 6 is an example of a display output on the displaying means from the equilibrium state analyzing apparatus according to Embodiment 1 of the present invention.

FIG. 6 shows the progress of the center of gravity fluctuation of a patient who underwent an operation of suture of skeletal muscles of a leg which was output and displayed in the outputting step s7 using the equilibrium state analyzing apparatus according to this embodiment. Thus, according to the equilibrium state analyzing apparatus of this embodiment, it is possible to make a daily observed comparison of the center of gravity fluctuation index using acceleration information.

Embodiment 2

Figure 7:
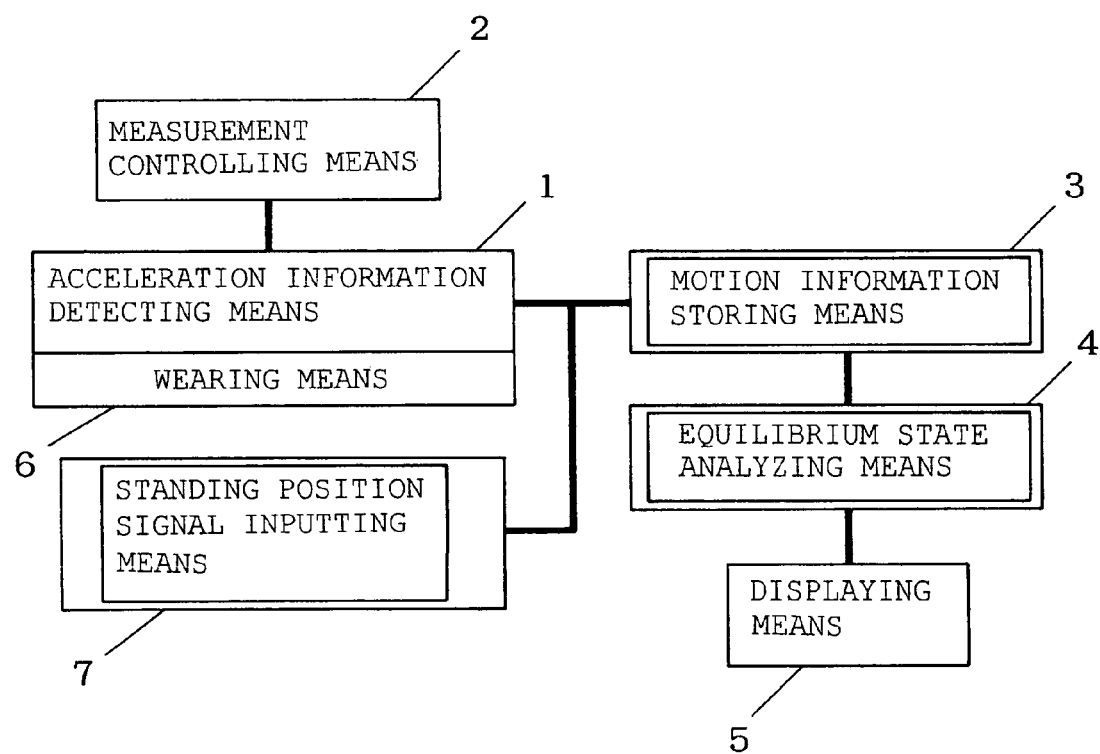
FIG. 7 is a block diagram of an equilibrium state analyzing apparatus according to Embodiment 2 of the present invention.
Figure 8:
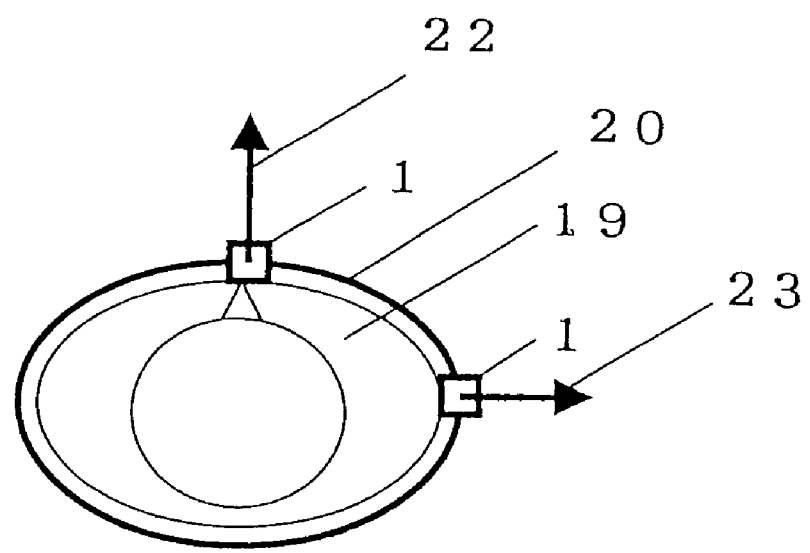
FIG. 8 illustrates an example of attaching acceleration information detecting means used for the equilibrium state analyzing apparatus according to Embodiment 2 of the present invention.

FIG. 7 is a block diagram of an equilibrium state analyzing apparatus according to Embodiment 2 of the present invention. Reference numeral 7 denotes standing position signal inputting means. According to this embodiment as shown in FIG. 8, acceleration information detecting means 1 is fixed close to the right iliac crest of the human body and abdomen by wearing means 6. FIG. 8 is a bird's eye view of the human body, reference numeral 19 in the figure denotes a human body, 20 denotes a belt-shaped wearing device wound around the human body, 22 denotes the frontward/backward direction (frontward is assumed to be a positive direction) of the human body, 23 denotes the rightward/leftward (rightward is assumed to be a positive direction) of the human body and 1 denotes acceleration information detecting means attached to the human body. The rest of the configuration is the same as that of Embodiment 1 and explanations thereof will be omitted.

According to this embodiment, in order to detect accelerations generated on the horizontal plane, the x-axis and y-axis which cross each other at right angles on the horizontal plane are assumed to be the frontward/backward direction and rightward/leftward direction of the human body respectively, and it is possible to detect accelerations in the respective directions. In this embodiment, one-axis acceleration sensor is used as the acceleration information detecting means 1, two acceleration information detecting means 1 are attached to the human body using the wearing device 20 as shown in FIG. 8. With this arrangement, accelerations generated on the horizontal plane caused by movement of the body are detected as voltage values, A/D-converted and then output as digital values.

The center of gravity fluctuation index output from the equilibrium state analyzing means 4 is the same as that in Embodiment 1.

Figure 9:
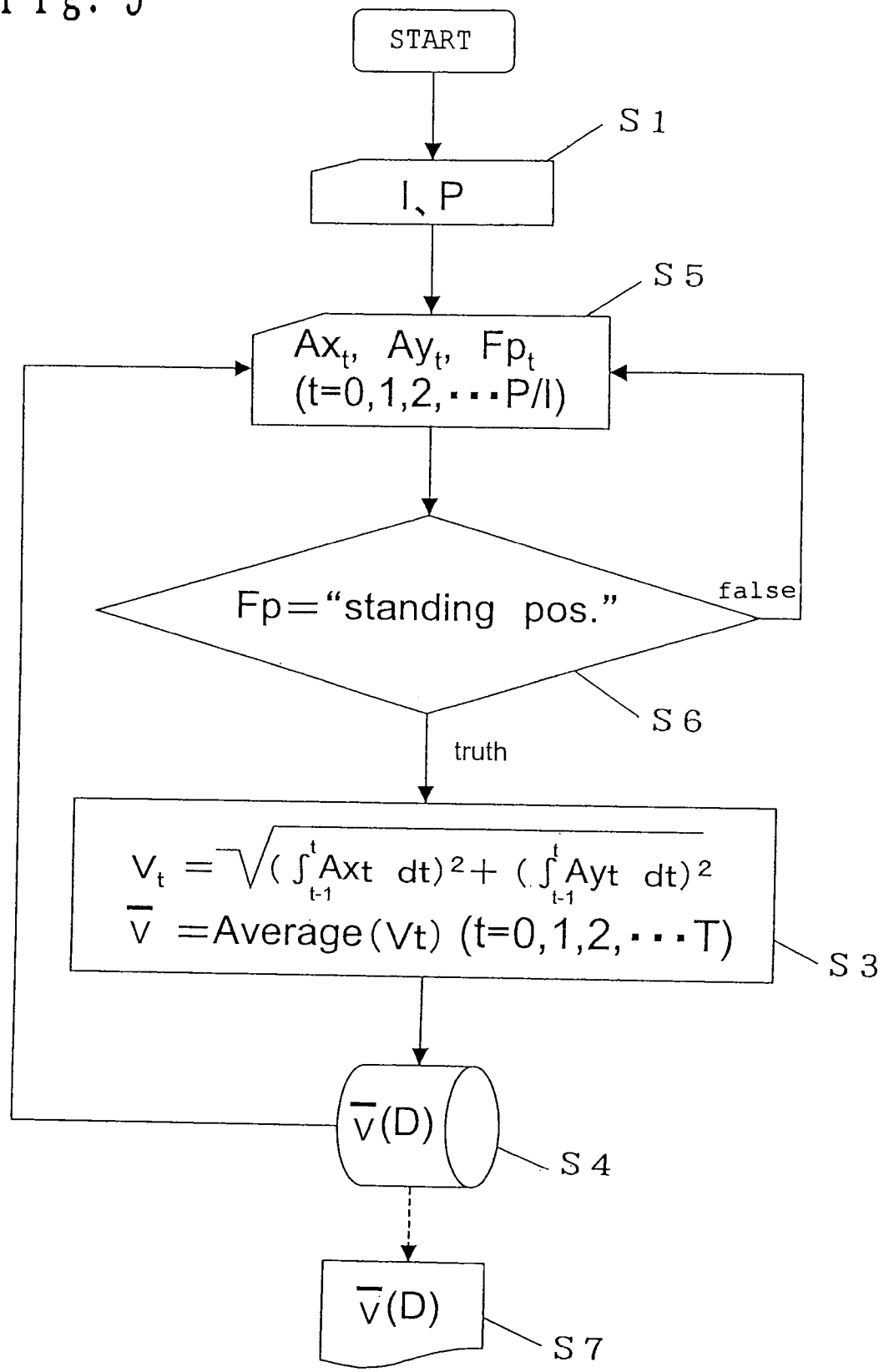
FIG. 9 is a flow chart showing an operation of the equilibrium state analyzing apparatus according to Embodiment 2 of the present invention.

An algorithm of the center of gravity fluctuation analysis in this embodiment is shown in FIG. 9. s1 denotes a measuring time setting step, s5 denotes a body information inputting step, s6 denotes a body information deciding step, s3 denotes a center of gravity fluctuation analyzing step, s4 denotes a motion information storing step and s7 denotes an outputting step.

In this embodiment, body information $Fp_t$ is input from the keyboard of a computer 8 and, for example, a character string "standing position" is assigned to a carriage return code and " " (space) is assigned to other key inputs and in this way data is entered. Furthermore, once the algorithm is started, the body information $Fp_t$ keeps body information $Fp_{t-1}$ which is the previous input unless further data is keyed in. Then, in the body information deciding step s6, a conditional branch is made depending on whether the body information $Fp_t$ is "standing posture" or not and if the result is true, the center of gravity fluctuation analyzing step 3 is executed and if the result is false, the body information inputting step s5 continues to be executed. Thus, according to the equilibrium state analyzing apparatus according to this embodiment, it is possible to make a daily observed comparison of the center of a gravity fluctuation index only using acceleration information in a standing position.

Embodiment 3

Figure 10:
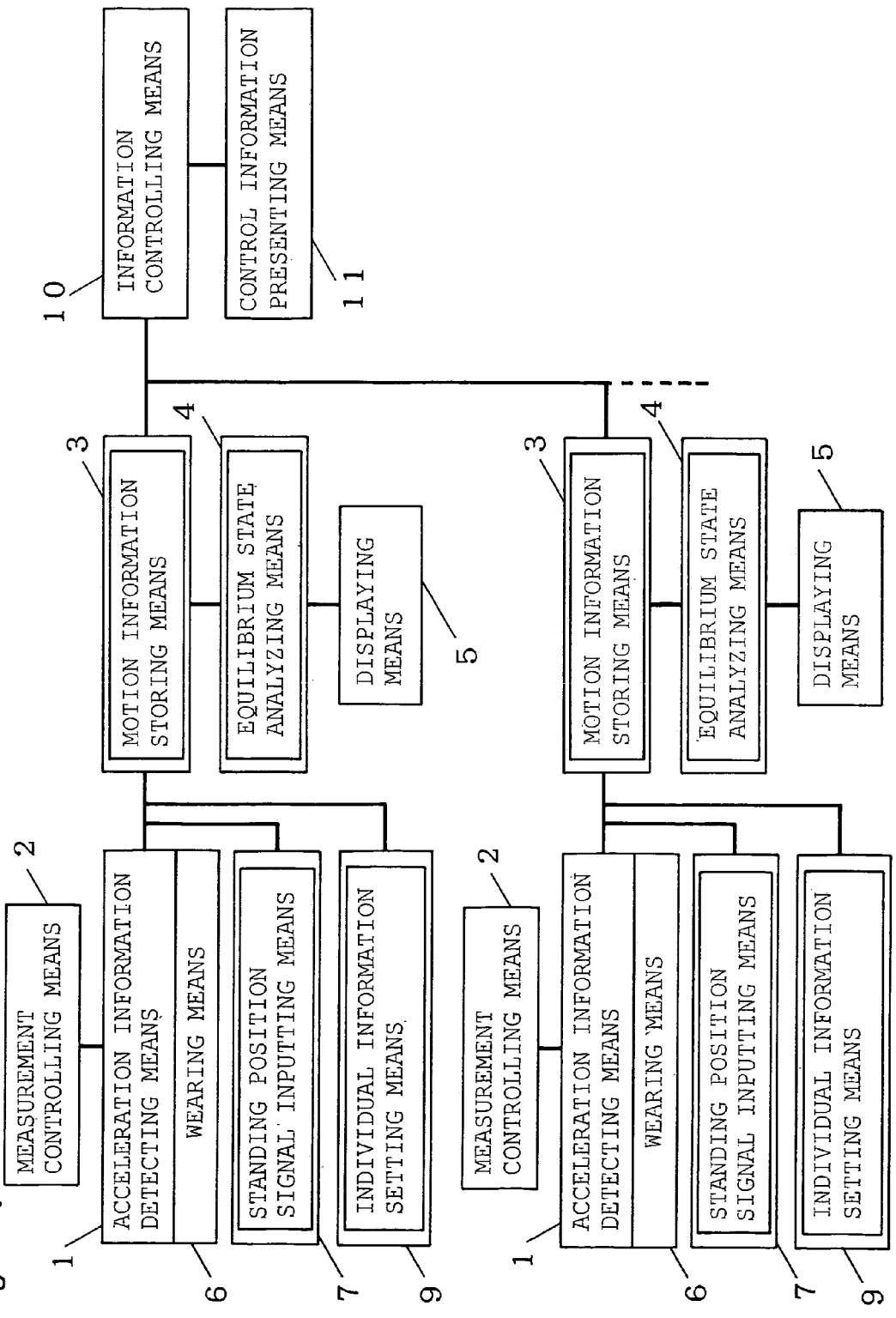
FIG. 10 is a block diagram of an equilibrium state analyzing apparatus according to Embodiment 3 of the present invention.
Figure 11:
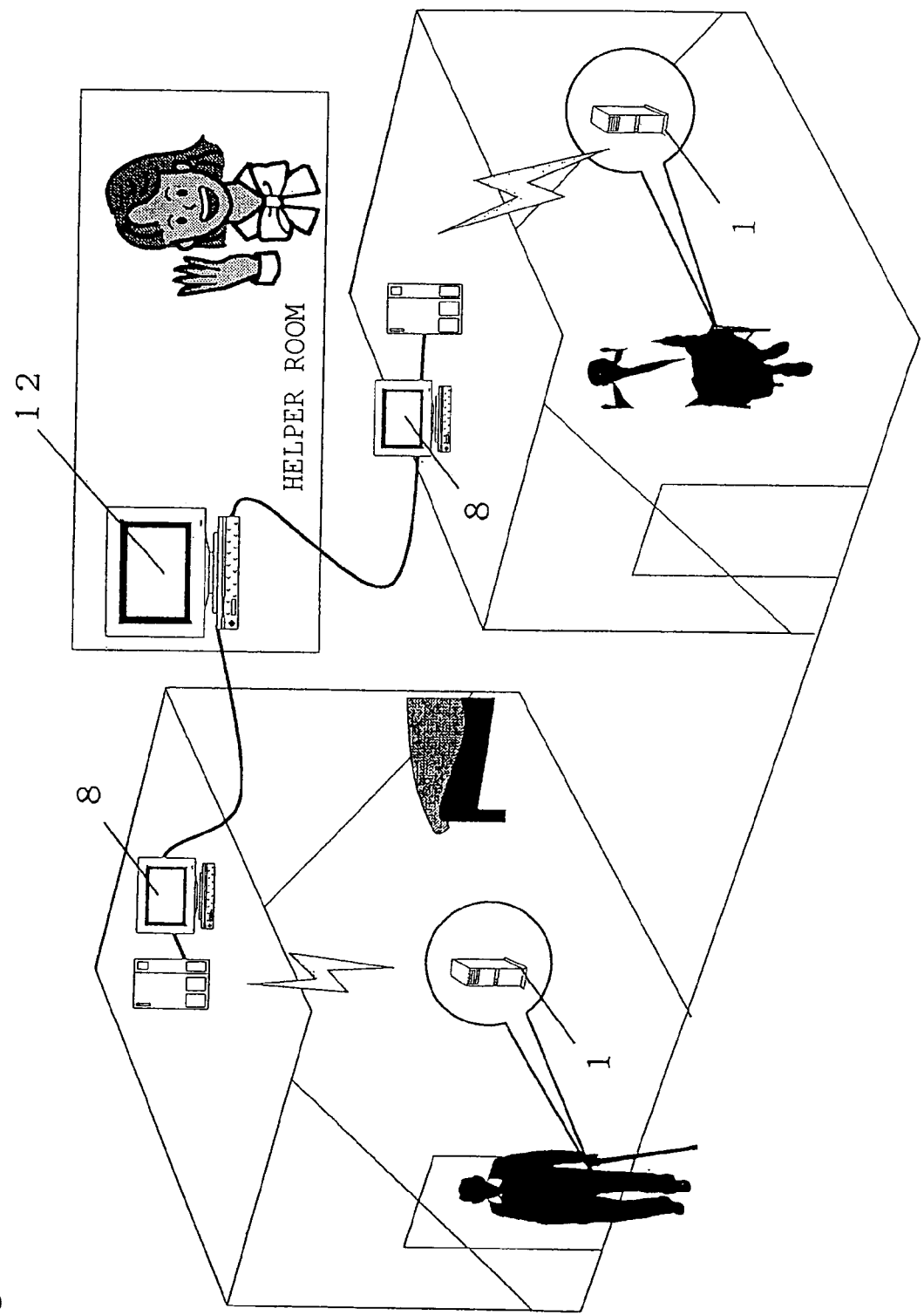
FIG. 11 illustrates a mode of use of the equilibrium state analyzing apparatus according to Embodiment 3 of the present invention.

FIG. 10 is a block diagram of an equilibrium state analyzing apparatus according to Embodiment 3 of the present invention. Reference numeral 9 denotes individual information setting means, 10 denotes information controlling means and 11 denotes control information presenting means. FIG. 11 shows an image of this embodiment.

In this embodiment as in the case of Embodiment 1, as shown in FIG. 11, acceleration information detecting means 1 is fixed to the waist of the human body, that is, close to the right iliac crest by wearing means 6. Furthermore, two axes (x-axis and y-axis) to be detected crossing each other at right angles on the horizontal plane are the same as those of Embodiment 1. The measurement controlling means 2, equilibrium state analyzing means 4, motion information storing means 3, displaying means 5, standing position signal inputting means 7 and individual information setting means 9 operate on a system based on a personal computer 8. As in the case of Embodiment 2, the equilibrium state analyzing means 4 operates only when posture information shows a standing position, inputs acceleration data from the acceleration information detecting means 1 on a time-series basis, calculates and outputs a center of gravity fluctuation index. Furthermore, at this time, calendar information output from the acceleration information detecting means 1 is stored in the motion information storing means 3 as ancillary information of the calculated center of gravity fluctuation index together with an ID number specific to an individual input from the individual information setting means 9.

The motion information storing means 3 stores a center of gravity fluctuation index together with an individual ID number and calendar information. The displaying means 5 presents the center of gravity fluctuation index stored in the motion information recording means 4 together with the calendar information which is ancillary information. The information controlling means 10 reads the center of gravity fluctuation indices and ancillary information stored in a plurality of or single motion information recording means 3 connected to a network, references the ID number and calendar information to thereby control the center of gravity fluctuation indices of a plurality of individuals over an extended period of time. Furthermore, the control information presenting means 11 can present time variations of a center of gravity fluctuation index for each ID number. The center of gravity fluctuation index output from the equilibrium state analyzing means 4 is the same as that in Embodiment 1. In this embodiment, a host computer 12 is used as the information controlling means 10 and control information presenting means 11. The host computer 12 secures a communication channel by means of the computer 8 and LAN assigned to an ID of each individual.

Thus, according to the equilibrium state analyzing apparatus of this embodiment, it is possible to make a daily observed comparison of a center of gravity fluctuation index using acceleration information only when a plurality of individuals are in a standing position and present the results.

Embodiment 4

Figure 12:
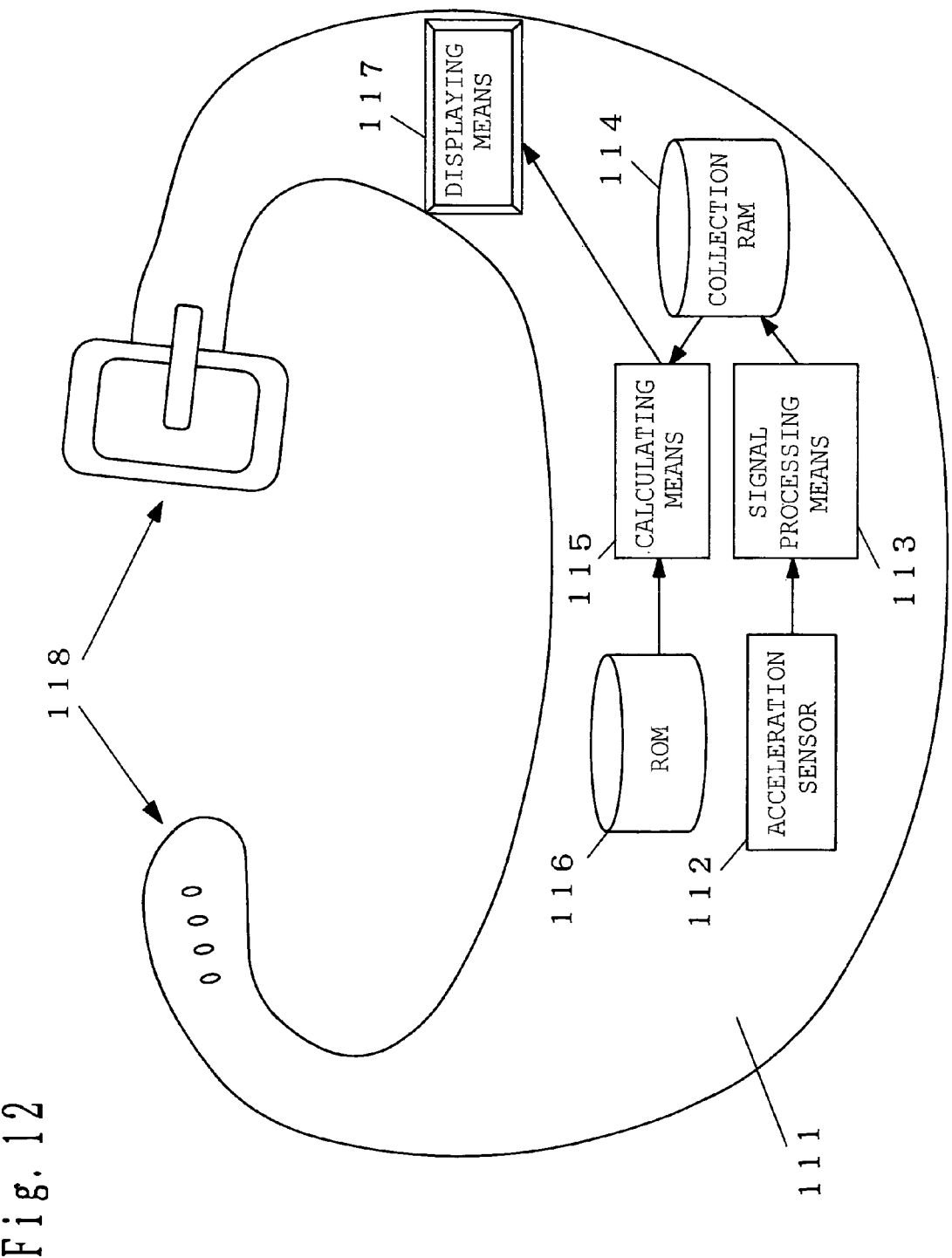
FIG. 12 is a schematic block diagram of an equilibrium state analyzing apparatus according to Embodiment 4 of the present invention.

An equilibrium state analyzing apparatus according to Embodiment 4 of the present invention will be explained with reference to drawings. FIG. 12 shows a schematic configuration of the equilibrium state analyzing apparatus of this embodiment.

FIG. 12 shows a configuration when an acceleration sensor is used as the system of the acceleration acquiring means in an equilibrium state analyzing apparatus 111.

The equilibrium state analyzing apparatus 111 comprises an acceleration sensor 112 (corresponds to as an example of the acceleration information detecting means of the present invention) that acquires acceleration information, a signal processing means 113 that processes output based on acceleration information obtained from the acceleration sensor 112, a collection RAM 114 that totalizes processing signals from the signal processing means 113, a calculating means 115 that ranks indices corresponding to the degree of fluctuation of the center of gravity by comparing the totalized signal with a predetermined threshold, a ROM 116 that stores thresholds and displaying means 117 that displays the calculation result of the calculating means 115.

The equilibrium state analyzing apparatus 111 is attached to the human body. Since it is attached to the waist which is the trunk of the human body, a dedicated holding member 118 may also be attached. The apparatus is illustrated here assuming that the entire equilibrium state analyzing apparatus 111 is attached, but the present invention is not necessarily limited to this. The acceleration sensor 112 must be placed at least at the waist and other parts need not always be attached to the waist.

As the human body fluctuates after fluctuation measurement is started, outputs are generated at the acceleration sensor 112. The signal processing means 113 A/D-converts analog signals output from the acceleration sensor 112 sequentially to digital outputs at a predetermined sampling rate. The converted digital outputs are totalized for a certain time and temporarily saved in the collection RAM 114. The calculating means 115 references the totalized output stored in the collection RAM 114 and at the same time references the threshold stored in the ROM 116 and ranks the degree of fluctuation of the human body. The calculation result is displayed on the displaying means 117.

Figure 13A:
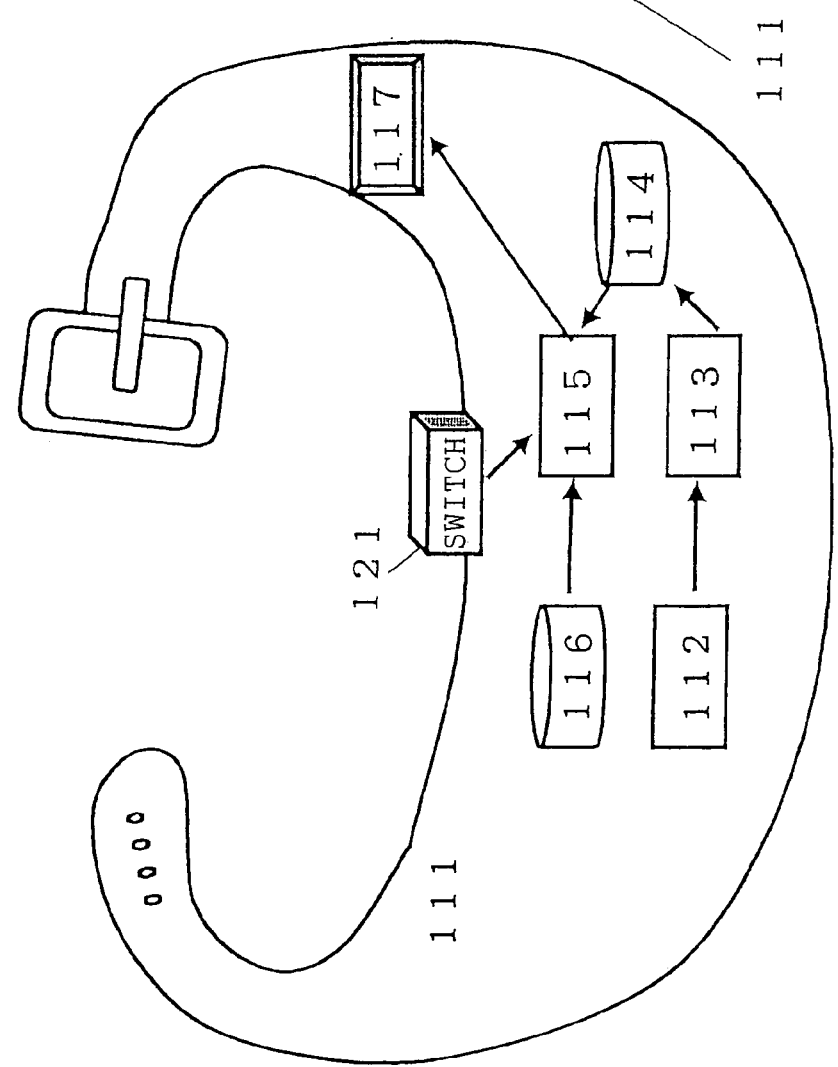
FIG. 13 illustrates an example of mode of use of the equilibrium state analyzing apparatus according to Embodiment 4 of the present invention.
Figure 13B:
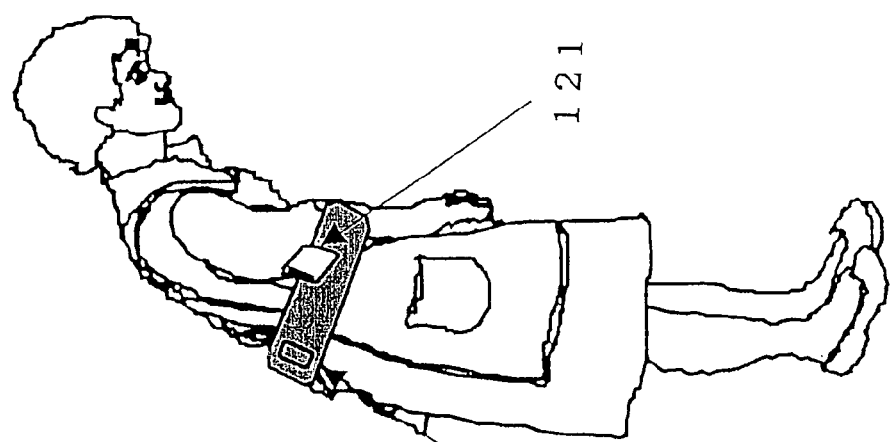

FIG. 13 shows the actual method of use of the equilibrium state analyzing apparatus 111. In the configuration shown in FIG. 13(*a*), a push switch 121 is further connected to the acceleration collection RAM 114 of the apparatus shown in FIG. 12 as signal inputting means. The user of this apparatus pushes the switch 121 based on the timing of detecting fluctuation of the center of gravity (see FIG. 13(*b*)). In synchronization with the input signal generated when the switch 121 is pressed, the acceleration collection RAM 114 starts to collect acceleration information. The collection start timing need not always be determined by a switch, but a sign indicating the collection start may also be displayed on the displaying means 117. Furthermore, it is also possible to provide a buzzer to inform that acceleration collection has completed.

FIGS. 14(*a*) and 14(*b*) show a template example for calculating fluctuation of the center of gravity at the center of gravity fluctuation calculating means 115. As shown in FIG. 14(*b*), a range 131 of the calculation result is segmented beforehand and ranking is made in comparison with the total of the collected acceleration output as shown in FIG. 14(*a*). The unit of values 20000–22000 in the ranking is an integral value. A greater integral value indicates a greater degree of fluctuation. Values 10 and 11 are shown only as examples.

Figure 15:
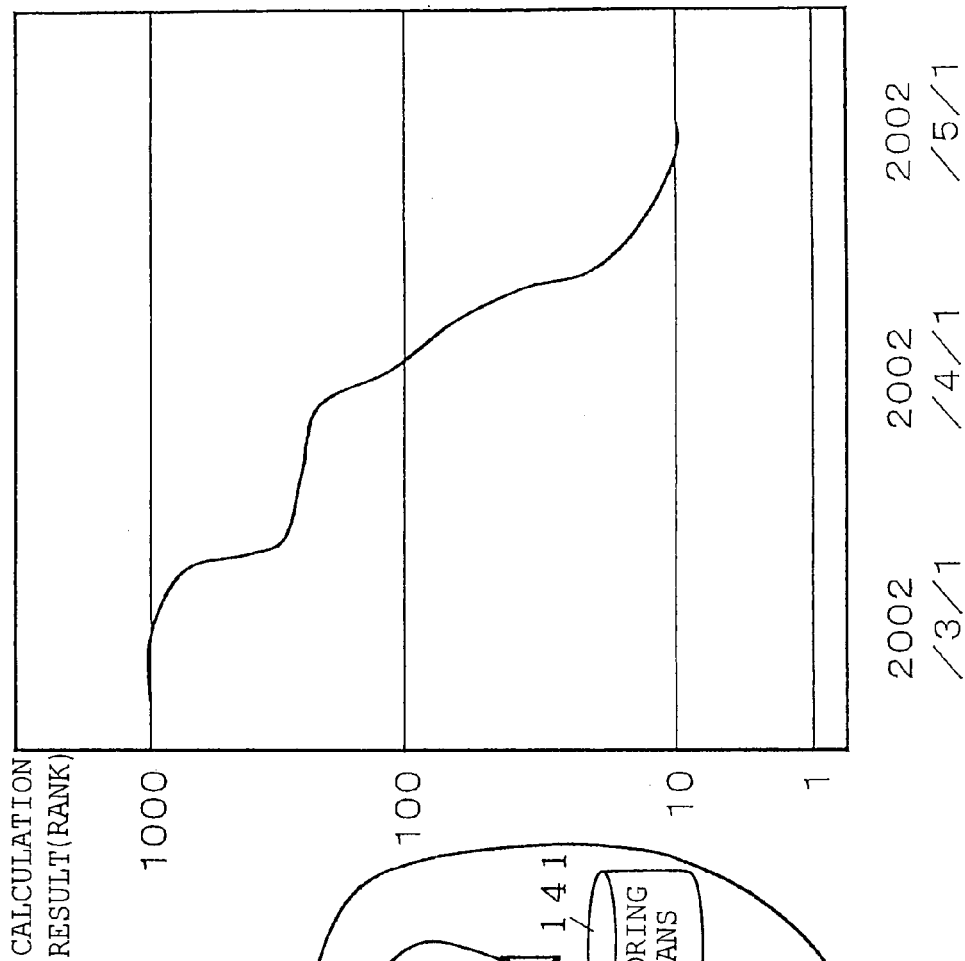
FIGS. 15(a) and 15(b) are schematic diagrams of a time-series variation of the equilibrium at the equilibrium state analyzing apparatus according to Embodiment 4 of the present invention.
Figure 15:
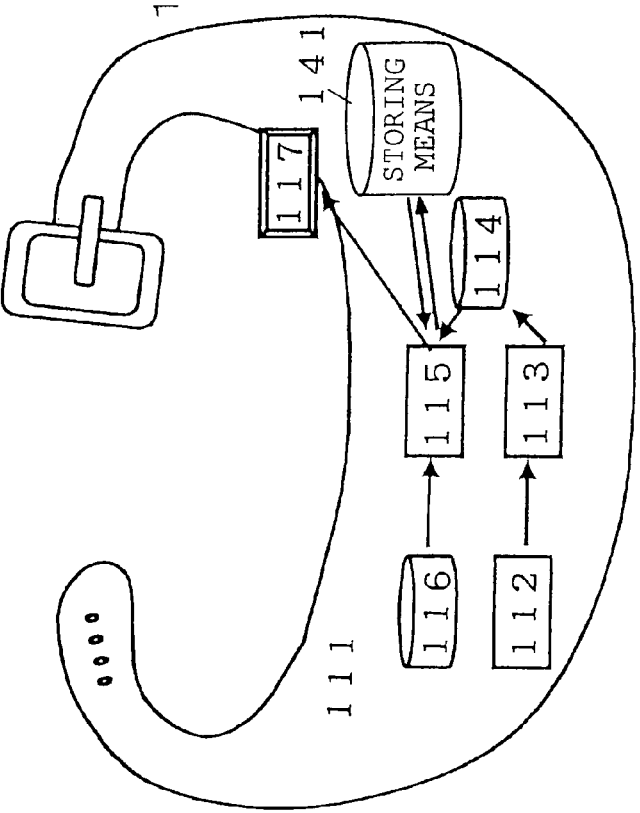

Furthermore, FIG. 15(*a*) shows the configuration in FIG. 12 with storing means 141 added and FIG. 15(*b*) is a schematic view showing a variation of ranking on a time-series basis. The figure shows an example of a case where a user in the process of rehabilitation of the leg uses the apparatus for an extended period of time and shows the daily progress of cure of the affected area. From this result, it is observed that the totalization result reduces gradually and the ranking level diminishes, and therefore it is evident that it is possible to prove with objective indices that the cure of the affected area is advancing favorably. Displaying this progress on the displaying means allows the patient or a doctor to comprehend the cure condition.

Embodiment 5

Figure 16:
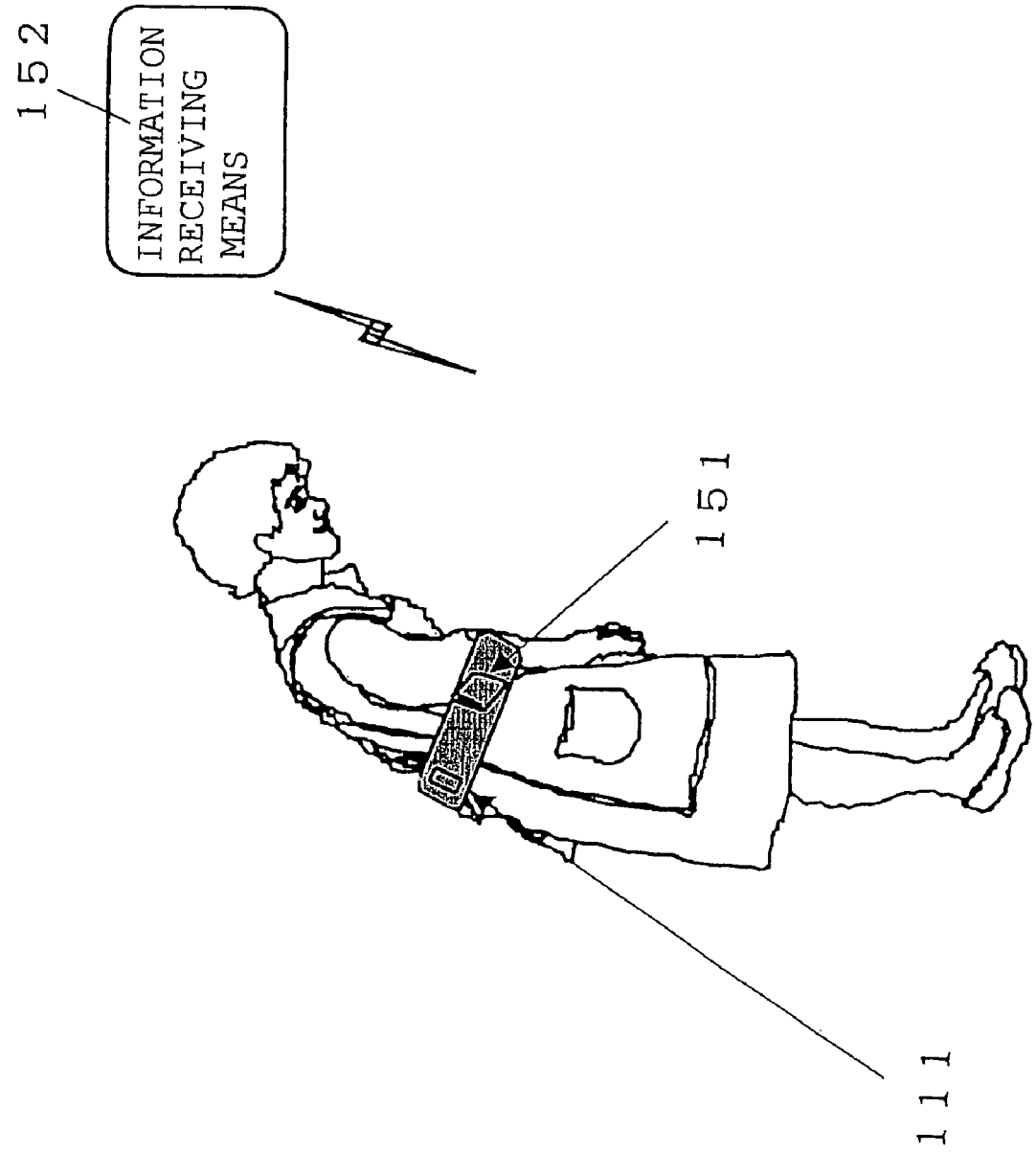
FIG. 16 is a schematic diagram of an equilibrium state detection system using an equilibrium state analyzing apparatus according to Embodiment 5 of the present invention.

An equilibrium state analysis system according to Embodiment 5 of the present invention will be explained with reference to the attached drawings. FIG. 16 shows a schematic configuration diagram of the equilibrium state analysis system of this embodiment. The configuration in this embodiment will be explained below.

This Embodiment 5 has a system configuration based on the equilibrium state analyzing apparatus 111 shown in FIG. 12 with the calculating means 115 further comprising information transmitting means 151 and information receiving means 152.

The equilibrium state analyzing apparatus 111 acquires and collects the user's acceleration information as in the case of FIG. 12 and calculates indices indicating fluctuation. The information on the calculated fluctuation is sent to the information receiving means 152 by the information transmitting means 151. By the information receiving means 152 receiving information on fluctuation of the center of gravity of the patient, it is possible for a family or doctor, etc., who stays in a remote place to know the progress of rehabilitation.

Embodiment 6

Figure 17:
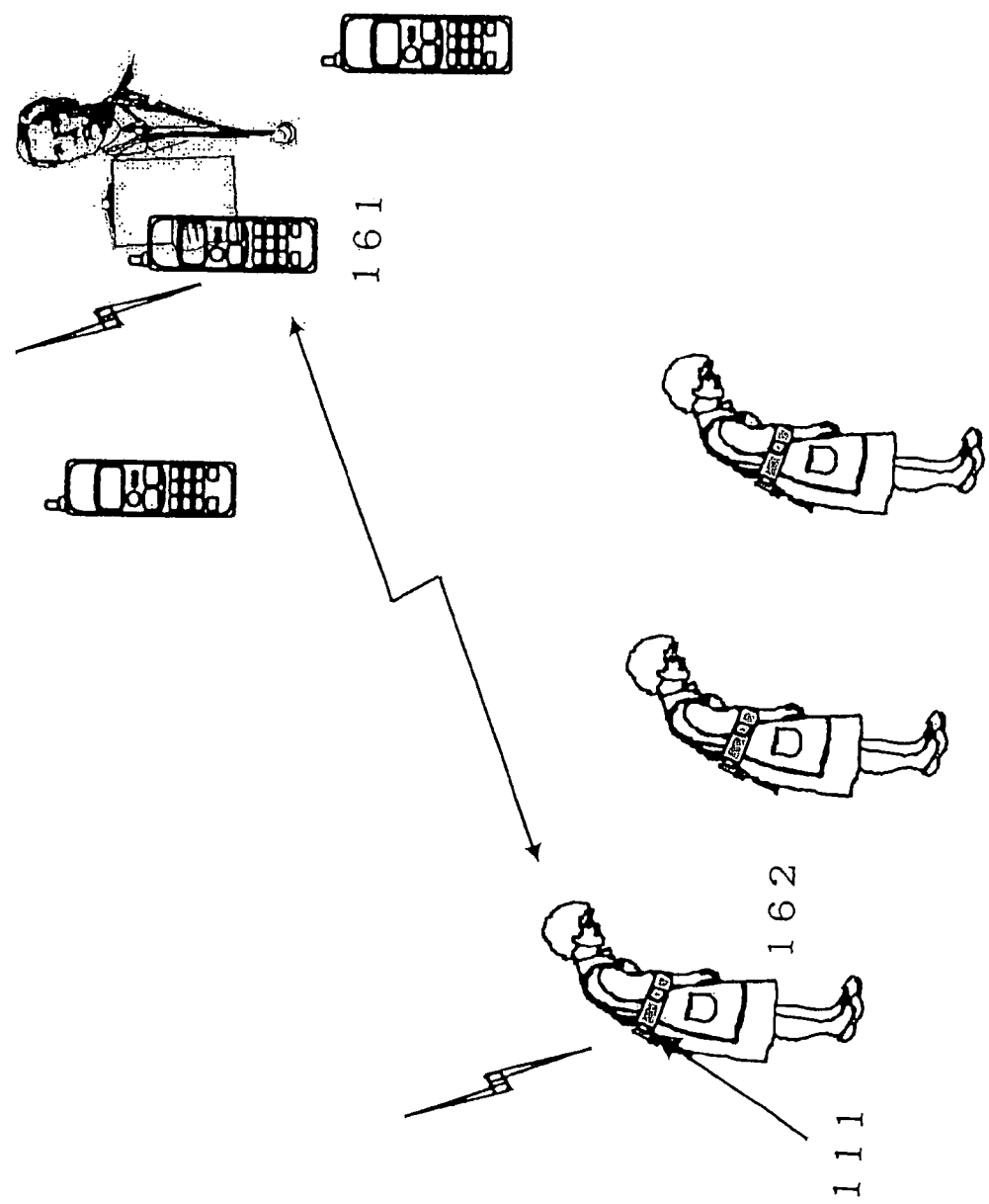
FIG. 17 is a schematic diagram of an equilibrium state detection system using an equilibrium state analyzing apparatus according to Embodiment 6 of the present invention.

An equilibrium state analysis system according to Embodiment 6 will be explained with reference to the attached drawings. FIG. 17 shows a schematic configuration diagram of the equilibrium state analysis system of this embodiment. The configuration of this embodiment will be explained below. FIG. 17 shows a case where a cellular phone 161 is used as information receiving means 152 and a plurality of users use the apparatus.

The information transmitting means 151 transmits the calculation result calculated by the calculating means 115 from the equilibrium state analyzing apparatus 111 attached to the users 162 to cellular phones owned by a doctor and family members, etc., registered beforehand by the users 162 individually. Through the cellular phones 161 which have received such information, it is possible to remotely comprehend the progress of rehabilitation of the users 162 using, for example, an independent ring tone or vibration function.

It is also possible to adapt this configuration so that a relay (not shown) is added, independent ID information is added to individual calculation results calculated by the equilibrium state analyzing apparatus 111, the relay holds transmission registration information and relays signals between the equilibrium state analyzing apparatus 111 and cellular phones 161, identifies the user 162 to whom the calculation result belongs and sends the information to individually registered cellular phones 161.

As is apparent from the above described explanations, according to the equilibrium state analysis systems in Embodiments 5 and 6, it is possible to realize an apparatus and system that detect the degree of fluctuation of the center of gravity for which no low-priced and compact method has existed to date.

Furthermore, since the apparatus is attached to the trunk of the body such as the waist, it is possible to approximate the position of acquired data to the actual center of gravity and also improve reliability of acquired information.

Furthermore, by further comprising storing means of storing calculation results on a time-series basis and displaying the storage result to the user and doctor, the present invention also functions effectively from the standpoint of general health care.

As the system of starting measurement of fluctuation of the center of gravity, it is also possible to adapt the configuration in such a way that signal inputting means such as a push button is further provided and the user starts the operation spontaneously or the start time is indicated by the displaying means.

Or it is also possible to adapt the configuration in such a way that the measurement end time is notified by means of a buzzer to clearly notify the measurer of the measurement end time. It is further possible to adopt a system in which the calculation result is automatically notified to a cellular phone, etc., owned by the doctor.

Embodiment 7

Figure 18:
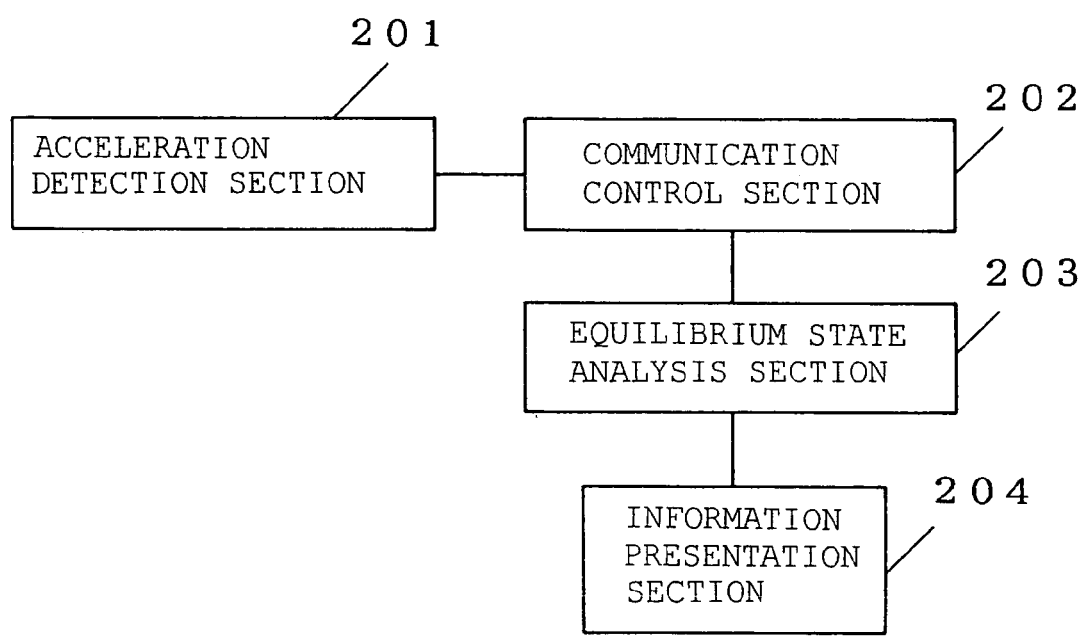
FIG. 18 is a block diagram of an equilibrium state analyzing apparatus according to Embodiment 7 of the present invention.

FIG. 18 is a block diagram of an equilibrium state analyzing apparatus according to Embodiment 7 of the present invention. Reference numeral 201 denotes an acceleration detection section which is an example of acceleration information detecting means, 202 denotes a communication control section, 203 denotes an equilibrium state analysis section, 204 denotes an information presentation section. The acceleration detection section 201 detects acceleration of the waist of the human body in at least one of frontward/backward directions, rightward/leftward directions and upward/downward (vertical) directions and outputs the acceleration of the human body to the equilibrium state analysis section 203 through the communication control section 202. The communication control section 202 assigns one channel to acceleration data in at least one direction or one channel to one acceleration detection section 201 to transmit acceleration data in a plurality of directions or outputs from a plurality of acceleration detection sections to one equilibrium state analysis section 203 by radio or using a cable.

The equilibrium state analysis section 203 stores the acceleration data input from the communication control section 202 for each channel on a time-series basis, stores the acceleration data as a series of waveform data and analyzes waveforms.

The information presentation section 204 presents the analysis result of the equilibrium state analysis section 203. This configuration allows a series of operations from an equilibrium state analysis on one examinee to presentation of the result.

Figure 19:
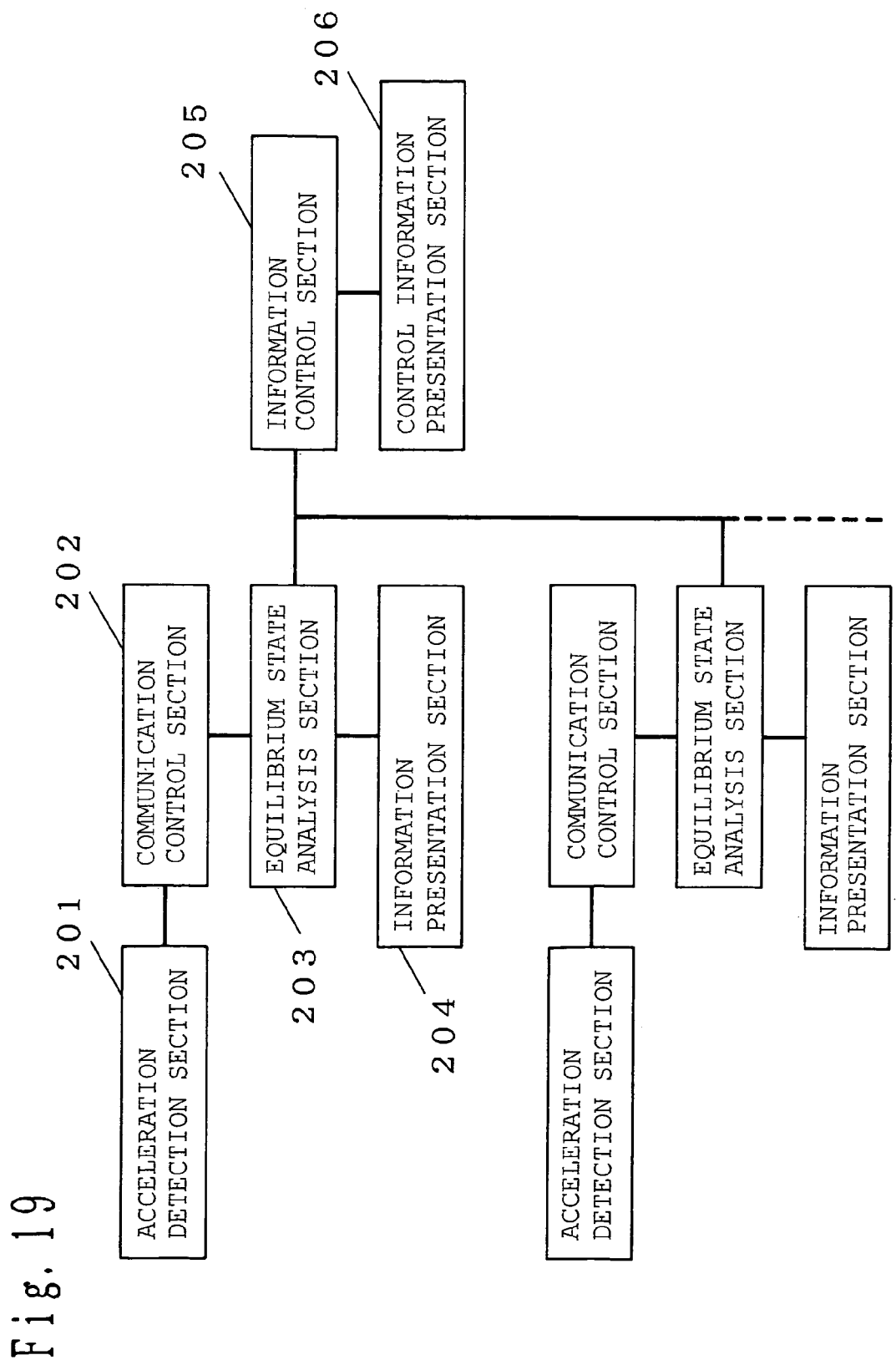
FIG. 19 is a block diagram of the equilibrium state analyzing apparatus according to Embodiment 7 of the present invention.

FIG. 19 is a block diagram to further illustrate details of the equilibrium state analyzing apparatus of this embodiment. The same components are assigned the same reference numerals. Reference numeral 205 denotes an information control section and 206 denotes a control information presentation section.

An acceleration detection section 1 detects acceleration of the waist of the human body in at least one of frontward/backward directions, rightward/leftward directions and upward/downward (vertical) directions and outputs the acceleration of the human body to the equilibrium state analysis section 203 through the communication control section 202. The communication control section 202 assigns one channel to acceleration data in at least one direction or one channel to one acceleration detection section to transmit acceleration data in a plurality of directions or outputs from a plurality of acceleration detection sections to one equilibrium state analysis section 203 by radio or using a cable. The equilibrium state analysis section 203 stores the acceleration data input from the communication control section for each channel on a time-series basis, stores the acceleration data as a series of waveform data and analyzes waveforms. The information presentation section 204 presents the analysis result of the equilibrium state analysis section 203.

The information control section 205 collects analysis results output from a plurality of equilibrium state analysis sections 203 according to a predetermined communication protocol, controls equilibrium state analysis results of a plurality of examinees all together and presents the control information through the control information presentation section 206.

Figure 20:
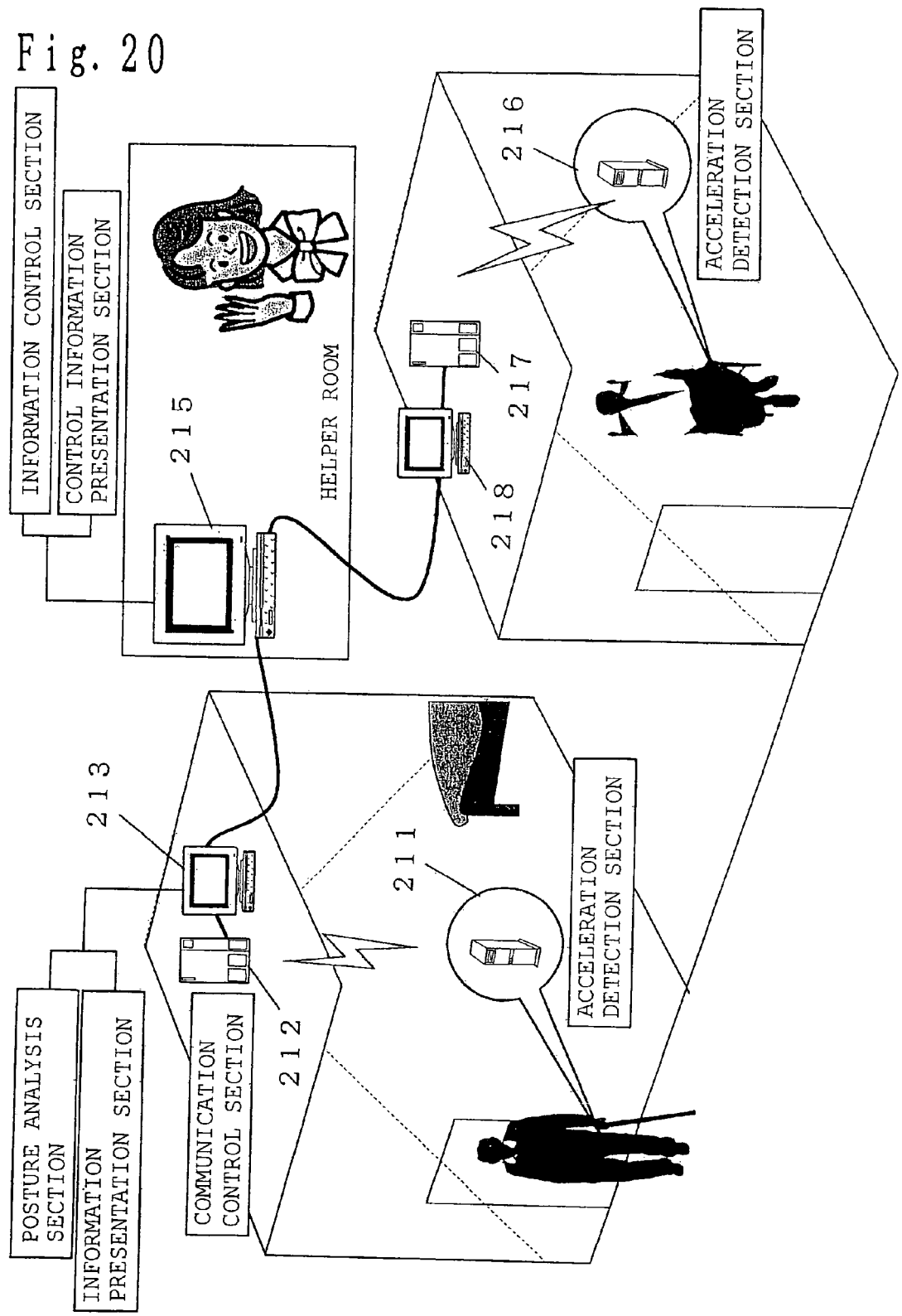
FIG. 20 is a schematic view illustrating a situation of use of the equilibrium state analyzing apparatus according to Embodiment 7 of the present invention.

FIG. 20 shows the equilibrium state analyzing apparatus according to this embodiment installed in a care house where a plurality of aged people live. Here, reference numeral 211 denotes an acceleration detection section, 212 denotes a communication control section, 213 denotes a personal computer including the equilibrium state analysis section 203 and information presentation section 204, 215 denotes a personal computer including an information control section and a control information presentation section, 216, 217 and 218 denote an acceleration detection section, communication control section and information presentation section respectively supplied to a second examinee.

Reference numerals 211 and 216 denote acceleration detection sections fixed at the height of the pelvis of the examinee by means of a wearing device, which detects accelerations of three axes in frontward/backward directions, rightward/leftward directions and upward/downward directions. The communication control sections 212 and 217 output accelerations of the human body to the equilibrium state analysis section 203 according to a predetermined communication protocol. The communication control section 202 assigns one channel to acceleration data in at least one direction and transmits acceleration data in three axis directions to the personal computers 213 and 218 by radio. The information control section included in the personal computer 215 collects data of the equilibrium state analysis section of the personal computer 213 according to a predetermined communication protocol as appropriate and presents the equilibrium state analysis result of each examinee to the staff of the care house. This configuration makes it possible to objectively and efficiently observe movements of a plurality of aged people in their daily life.

Figure 21:
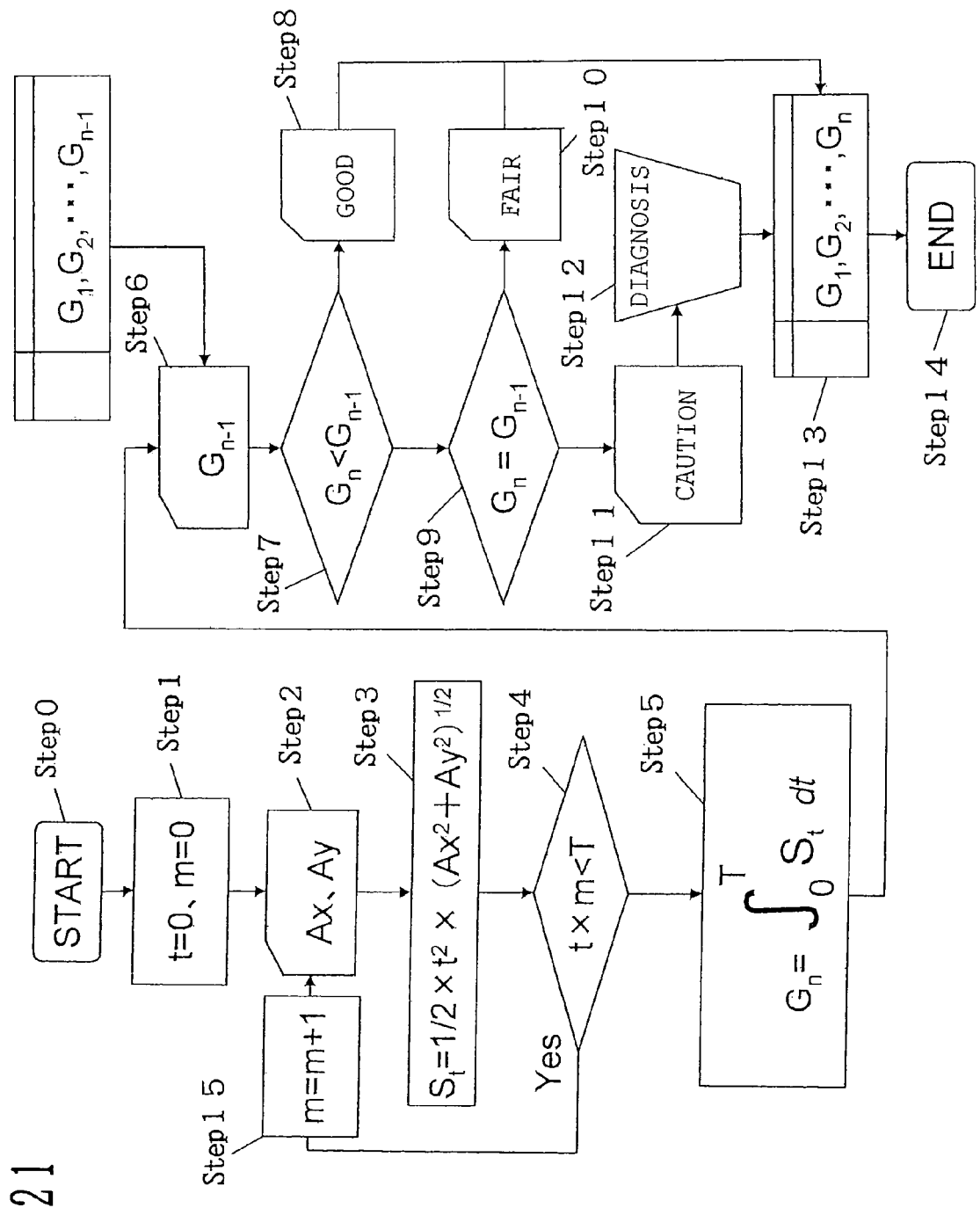
FIG. 21 illustrates an operation flow of the equilibrium state analyzing apparatus according to Embodiment 7 of the present invention.

FIG. 21 shows a flow of the equilibrium state analysis method according to this embodiment shown in FIG. 20. This is an example of an equilibrium state analysis method and the equilibrium state analysis method in the equilibrium state analysis section 203 is intended to calculate fluctuation of the center of gravity from accelerations in frontward/backward directions and accelerations in rightward/leftward directions with respect to the human body in a standing position. That is, an equilibrium state analysis confirms that the examinee is in a normal static standing position, starts an equilibrium state analysis at a predetermined opportunity (Step 0), starts counting simultaneously with the start of the analysis, resets a counter (m) (Step 1), inputs acceleration (Ax) in the rightward/leftward direction and acceleration (Ay) in frontward/backward direction in Step 2 and calculates a center of gravity position ($S_t$) at a predetermined time interval (t) from Step 0 in Step 3. Steps 2 to 4 are repeated until the processing in Step 3 reaches a predetermined time (T). When the processing in Step 3 reaches a predetermined count, the position of the center of gravity ($S_t$) is integrated for a section from t=0 to t=T in Step 5 and the integral value is substituted into a center of gravity fluctuation index ($G_n$) The above expression is shown in (Formula 2).

$$S_t = 1/2 \times t^2 \times (Ax^2 + Ay^2)^{1/2} \quad \text{(Formula 2)}$$

$$G_n = \int_0^T S_t \, dt$$

The equilibrium state analysis section 203 contains stored data ($G_1, G_2, \ldots, G_{n-1}$) and inputs the latest center of gravity fluctuation index ($G_{n-1}$) of the above described stored data in Step 6 and compares it with the latest center of gravity fluctuation index ($G_n$) in Step 7. When $G_n$ is smaller than $G_{n-1}$, the equilibrium state analysis section 203 decides that the deviation of the center of gravity is improving (Step 7), outputs a message "good trend" (Step 8) and uses it as reference data in the future (Step 13). When $G_n$ is equal to $G_{n-1}$, the equilibrium state analysis section 203 decides that the deviation of the center of gravity is kept (Step 9), outputs a message "fair" (Step 10) and uses it as reference data in the future (Step 13). In other cases, the equilibrium state analysis section 203 decides that the deviation of the center of gravity is deteriorating and decides it to be a state requiring caution (Step 11). In this case, the data is passed to judgment by the staff (Step 12) and then used as reference data in the future (Step 13). When Step 13 completes, the predetermined equilibrium state analysis completes.

Figure 22:
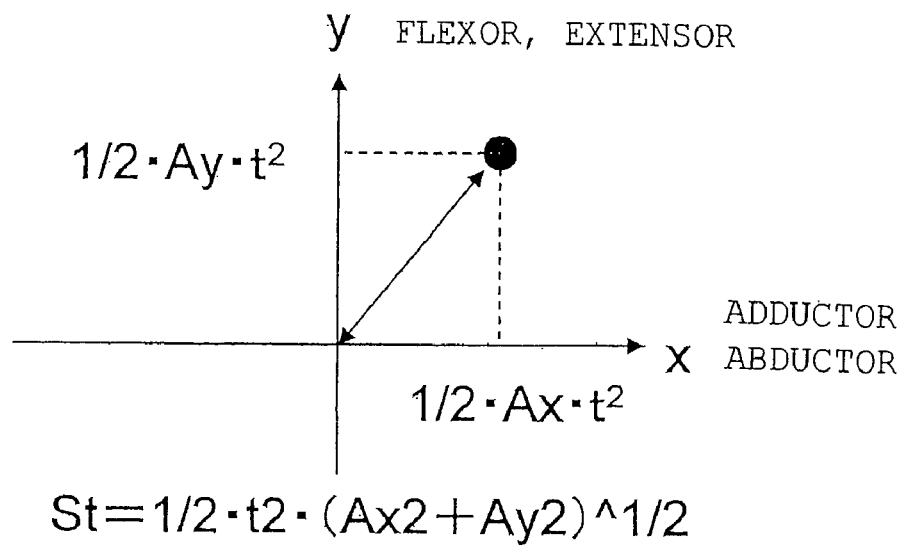
FIG. 22 illustrates a relationship between the position of the center of gravity on the horizontal plane, accelerations in frontward/backward direction and rightward/leftward direction at an arbitrary time in the flow of motion analysis of the equilibrium state analyzing apparatus according to Embodiment 7 of the present invention.

FIG. 22 shows the position of the center of gravity projected onto the horizontal plane at time t when the position of the center of gravity at t=0 is assumed to be the origin in the flow of the equilibrium state analysis and shows a relationship between the distance (that is, displacement ($S_t$)) from the origin and acceleration (Ax) in the rightward/leftward direction and acceleration (Ay) in frontward/backward direction.

Figure 23:
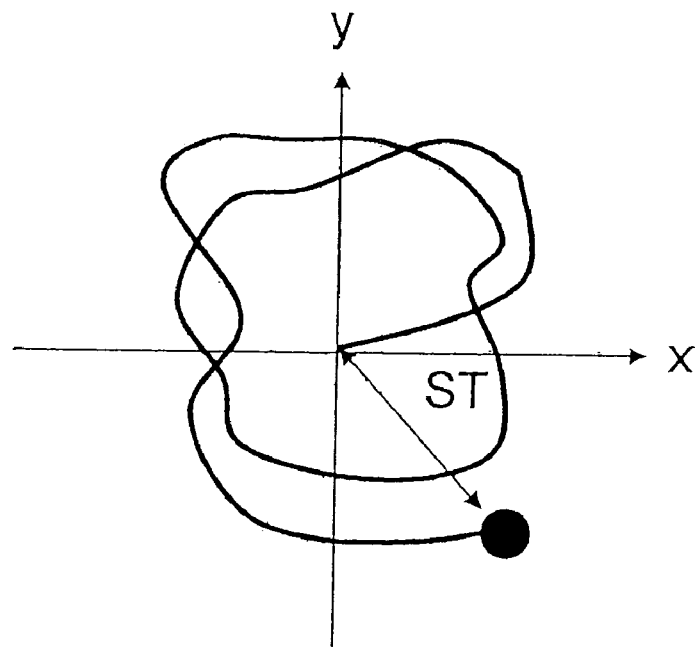
FIG. 23 illustrates a track of the center of gravity from the start of an analysis to a predetermined time at the equilibrium state analyzing apparatus according to Embodiment 7 of the present invention.

FIG. 23 shows a track of $S_t$ from t=0 to predetermined time T and shows that the center of gravity fluctuation index ($G_n$) in Step 5 corresponds to the amount of center of gravity fluctuation.

Using the data projected onto the horizontal plane as $S_t$ allows a simple way of providing support to prevent falling which is a primary cause for a bedridden life rather than an analysis of a three-dimensional equilibrium state. When, of the envelope including all the contact surfaces or contact points of the human body located on the horizontal plane, a plane having an envelope whose circumference is shortest as the circumference is assumed to be a support base and the line projected from the center of gravity of the human body in the vertical direction is assumed to be the line of the center of gravity, the stability of the human body is generally maintained by the line of the center of gravity passing within the support base and increases when the area of the support base is relatively large with respect to the height of the center of gravity and when the line of the center of gravity passes through the center of the support base.

Therefore, the stability of the human body can be evaluated from a positional relationship between the support base determined by the positions at which both legs contact the ground and an intersection between the line of the center of gravity and horizontal plane. $S_t$ of this embodiment is a point projected onto the horizontal plane, which approximates an intersection between the line of the center of gravity and horizontal plane, and it is possible to evaluate the stability from the correlation between $S_t$ and the basal surface by setting a certain area on the horizontal plane and using the area as a provisional basal surface.

Figure 26:
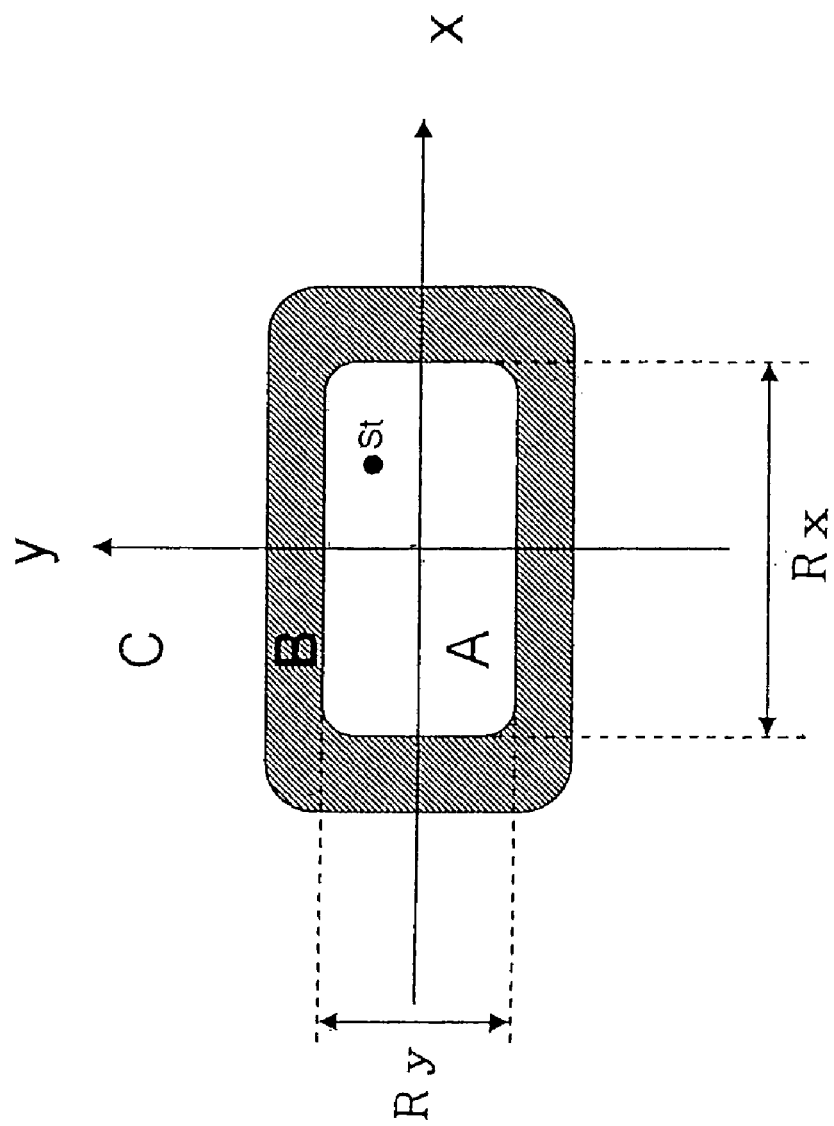
FIG. 26 illustrates an example of a basal surface set on the coordinate plane shown in FIG. 22.

FIG. 26 is an example of the basal surface set on the coordinate plane shown in FIG. 16. In the case of FIG. 26, the origin of the coordinate axes coincides with the center of the basal surface. Symbols A, B and C in FIG. 26 denote areas and area A is a basal surface provisionally set from the shoulder width (Rx) and the length of the foot in the longitudinal-axis direction (Ry). When $S_t$ exists in this area, the posture can be maintained. Area B is an area resulting from expanding area A in respective directions at a predetermined rate (approximately 130% in this embodiment) depending on the individual and when St exists in this area, it is necessary to change the posture such as positions of the feet to avoid falling. C represents other areas and when St exists in this area, it is impossible to maintain the standing position, that is, falling is unavoidable. The posture in the standing position can be maintained by St being outside the area C. That is, when St is included only in area A, it is a static standing position and has the highest posture maintaining performance and when St also exists in area B, it includes a herald that St will move to area C. Thus, setting predetermined conditions for a correlation between Stand basal surface makes it possible to predict falling and support prevention of falling.

Figure 24:
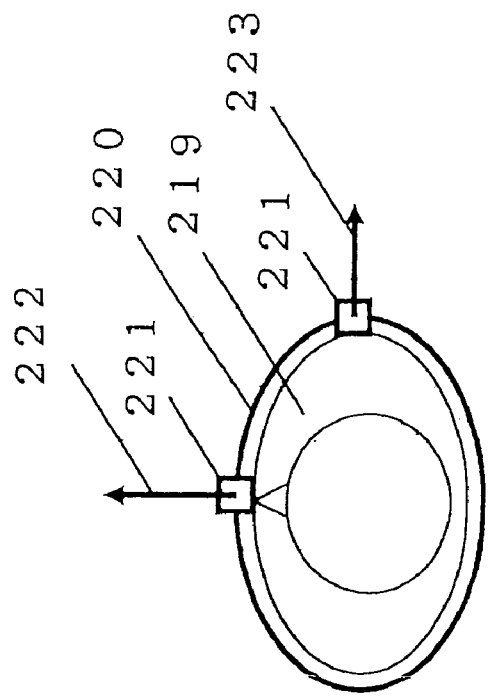
FIG. 24 illustrates a positional relationship between a wearing device at the height of the pelvis of the human body in a standing position and an acceleration detection section of the equilibrium state analyzing apparatus according to Embodiment 7 of the present invention.

FIG. 24 shows a positional relationship between the wearing device and the acceleration detection section at the height of the pelvis of the human body in a standing position. Reference numeral 219 denotes the human body viewed from above, 220 denotes an acceleration detection section wearing device, 221 denotes acceleration detection sections that detect acceleration in only one direction or two directions, 222 denotes the frontward (positive) direction of the acceleration in the frontward/backward directions detected by the acceleration detection section 221 and 223 denotes the rightward (positive) direction of the acceleration in the rightward/leftward directions detected by the acceleration detection section 221.

When the acceleration detection section 221 detects accelerations in two directions, if the other axis of acceleration to be detected is set in the vertical direction in this figure, it is possible to detect accelerations on three axes using a two-axis acceleration sensor.

Figure 25:
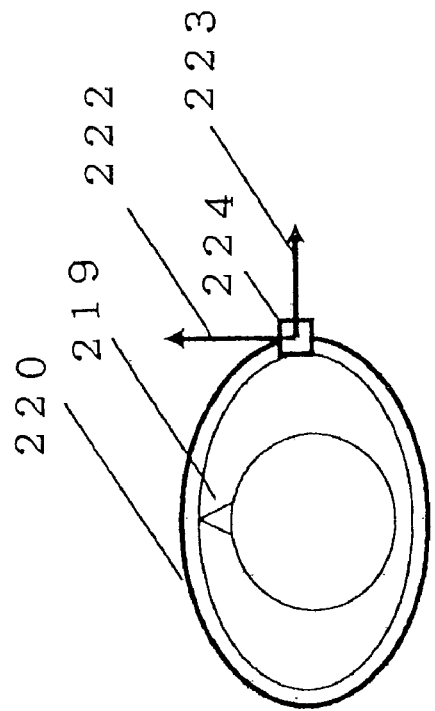
FIG. 25 illustrates a positional relationship between a wearing device at the height of the pelvis of the human body in a standing position and an acceleration detection section of the equilibrium state analyzing apparatus according to Embodiment 7 of the present invention.

FIG. 25 shows another example of a positional relationship between the wearing device and acceleration detection section 224 at the height of the pelvis of the human body in a standing position. Reference numeral 224 denotes an acceleration detection section that detects accelerations in two or three directions.

As far as the acceleration detection sections 221 and 224 are held at the height of the pelvis in a standing position and they can detect acceleration in at least one of frontward/backward directions, rightward/leftward directions and upward/downward directions to the human body in a standing position, they are limited to no other positional conditions.

The equilibrium state analyzing apparatus according to this embodiment can extend the area of measuring motions of the center of gravity of the human body into a home and analyze basic motions such as walking and falling other than so-called fluctuation of the center of gravity.

In the above explanations, the acceleration information detecting means of the present invention is fixed to the waist of the human body, that is, close to the iliac crest or abdomen by means of the wearing means 6, but the acceleration information detecting means of the present invention is not limited to the above example and can detect fluctuation of the center of gravity of the human body if it is attached to the trunk of the human body and can thereby achieve similar effects as those described above.

The program of the present invention is a program for causing a computer to execute the functions of all or some means (or apparatuses and elements, etc.) of the above described equilibrium state analyzing apparatus of the present invention and is a program that operates in cooperation with the computer.

Furthermore, the recording medium of the present invention is a recording medium storing a program for causing a computer to execute all or some functions of all or some means (or apparatuses and elements, etc.) of the above described equilibrium state analyzing apparatus of the present invention and is a recording medium which is computer-readable and allows the read program to execute the above described functions in cooperation with the computer.

The above described "some means (or apparatuses and elements, etc.)" of the present invention denotes one or several means out of the plurality of the respective means.

Furthermore, the above described "functions of means (or apparatuses and elements, etc.)" of the present invention denotes all or some functions of the respective means.

Furthermore, one mode of use of the program of the present invention can also be a mode in which the program is recorded in a computer-readable recording medium and operates in cooperation with the computer.

Furthermore, one mode of use of the program of the present invention can also be a mode in which the program is transmitted through a transmission medium, read by a computer and operates in cooperation with the computer.

The data structure of the present invention includes a database, data format, data table, data list and type of data, etc.

Furthermore, the recording medium includes a ROM, etc., and the transmission medium includes a transmission medium such as the Internet, light, radio wave and sound wave, etc.

Furthermore, the above described computer of the present invention is not limited to pure hardware such as CPU, but can include firmware, OS, or peripheral devices.

As described above, the configuration of the present invention can be implemented by software or hardware.

The equilibrium state analyzing apparatus, equilibrium state analysis method, program thereof and recording medium according to the present invention are characterized by placing few constraints on the degree of freedom in the area of motion or posture of the examinee and it is useful as an equilibrium state analyzing apparatus and equilibrium state analysis system, etc.

The invention claimed is:

1. An equilibrium state analyzing apparatus comprising:
   acceleration information detecting means, attached to a trunk of a human body, of detecting at least one linear accelerations generated within the horizontal plane by time sampling of the linear acceleration in a measuring period;
   motion information storing means of storing said detected accelerations; and
   equilibrium state analyzing means of analyzing the equilibrium state of the human body by integrating said stored acceleration information, wherein the equilibrium state analyzing means calculates and outputs an average velocity during the measuring period by integration of the time-sampled acceleration.

2. The equilibrium state analyzing apparatus according to claim 1, wherein said acceleration information detecting means detects accelerations generated in the x- and y-directions which cross each other at right angles within the horizontal plane, and
   said equilibrium state analyzing means calculates and outputs velocities by integrating acceleration generated in said x-direction and acceleration generated in said y-direction, respectively.

3. The equilibrium state analyzing apparatus according to claim 1, wherein the equilibrium state analyzing means outputs the stored totalized acceleration information corresponding to the time from a start to an end of a measurement of acceleration.

4. The equilibrium state analyzing apparatus according to claim 3, further comprising a display device of displaying the output data, wherein the motion information storing means stores the totalized acceleration and measured date data and the equilibrium state analyzing means outputs the totalized acceleration corresponding to the date data stored in the motion information storing means to the displaying means over time.

5. The equilibrium state analyzing apparatus according to claim 3, wherein the equilibrium state analyzing means ranks the totalized acceleration information.

6. The equilibrium state analyzing apparatus according to claim 1, further comprising standing position signal inputting means, connected to the equilibrium state analyzing means, of inputting a standing position signal, wherein the equilibrium state analyzing means starts an analysis of the equilibrium state when the standing position signal is input to the standing position signal inputting means.

7. A program for operating a computer as the motion information storing means of storing the detected acceleration and the equilibrium state analyzing means of analyzing the equilibrium state of the human body by integrating the stored acceleration information in the equilibrium state analyzing apparatus according to claim 1.

8. A recording medium which stores the program according to claim 7 and which is configured to be processed by a computer.

9. The equilibrium state analyzing apparatus according to claim 1, wherein the equilibrium state analyzing means totalizes the stored acceleration information and ranks the totalized acceleration information based on an index of ranges, the totalized acceleration information corresponding to a time from a start to an end of a measurement of an acceleration.

10. An equilibrium state analyzing apparatus comprising:
acceleration information detecting means, attached to the trunk of the human body, of detecting accelerations generated in at least one direction within the horizontal plane;
motion information storing means of storing said detected accelerations; and
equilibrium state analyzing means of analyzing the equilibrium state of the human body by integrating said stored acceleration information, wherein said acceleration information detecting means detects accelerations generated in the x- and y-directions which cross each other at right angles within the horizontal plane, and
said equilibrium state analyzing means calculates and outputs velocities by integrating the acceleration generated in said x-direction and the acceleration generated in said y-direction, respectively, said velocity (Vt) being determined from the expression:

$$V_t = \sqrt{\left(\int_{t-1}^{t} Axt\,dt\right)^2 + \left(\int_{t-1}^{t} Ayt\,dt\right)^2}$$

$$\overline{V} = \text{Average}(Vt) \qquad (t = 0, 1, 2, \ldots T)$$

where Axt is the acceleration in said x-direction, Ayt is the acceleration in said y-direction (t is a sampling timing, t=0, 1, 2 . . . P/I, P is a measuring time and I is a sampling interval) and said equilibrium state analyzing means calculates and outputs an average velocity over the measuring time P from said calculated velocity (Vt).

11. The equilibrium state analyzing apparatus according to claim 10, further comprising a display device of displaying said output data,
wherein said motion information storing means stores said calculated average velocity and measured date data, and
said equilibrium state analyzing means displays said calculated average velocity corresponding to said date data stored in said motion information storing means on said display device over time.

12. An equilibrium state analyzing apparatus comprising:
acceleration information detecting means, attached to the trunk of the human body, of detecting accelerations generated in at least one direction within the horizontal plane;
motion information storing means of storing said detected accelerations; and
equilibrium state analyzing means of analyzing the equilibrium state of the human body by integrating said stored acceleration information, wherein said acceleration information detecting means detects accelerations generated in the x- and y-directions which cross each other at right angles within the horizontal plane, and
said equilibrium state analyzing means calculates and outputs velocities by integrating the acceleration generated in said x-direction and the acceleration generated in said y-direction, respectively, the equilibrium state analyzing apparatus further comprising individual information setting means of setting individual-specific IDs and information controlling means of controlling the output from the equilibrium state analyzing means corresponding to each ID, wherein the output from the equilibrium state analyzing means corresponding to each ID is provided as an index.

13. An equilibrium state analyzing apparatus comprising:
acceleration information detecting means, attached to the trunk of the human body, of detecting accelerations generated in at least one direction within the horizontal plane; motion information storing means of storing said detected accelerations; and
equilibrium state analyzing means of analyzing the equilibrium state of the human body by integrating said stored acceleration information, wherein the acceleration information detecting means detects accelerations generated in the x- and y-directions which cross each other at right angles within the horizontal plane, the equilibrium state analyzing means calculates and outputs displacement in the center of gravity of the human body by integrating the acceleration generated in the x-direction and the acceleration generated in the y-direction twice respectively.

14. The equilibrium state analyzing apparatus according to claim 13, wherein the displacement (St) and the center of gravity fluctuation index (Gn) (n: measuring count) are determined from the expression:

$$S_t = 1/2 \times t^2 \times (Ax^2 + Ay^2)^{1/2}$$

$$G_n = \int_0^T S_t\,dt$$

where Axt is the acceleration in the x-direction, Ayt is the acceleration in the y-direction (t is a sampling timing, t=0, 1, 2 . . . P/I, P is a measuring time and I is a sampling interval), and the equilibrium state analyzing means outputs the calculated displacement and the center of gravity fluctuation index.

15. The equilibrium state analyzing apparatus according to claim 14, wherein the equilibrium state analyzing means compares the calculated Gn with G1, G2, . . . Gn−1 and outputs "good" when Gn<Gn−1 and outputs "fair" when Gn=Gn−1 and outputs "caution" when Gn>Gn−1.

16. The equilibrium state analyzing apparatus according to claim 14, wherein the equilibrium state analyzing means decides that the body is in a stationary standing position when the displacement is within a predetermined area from a position of the center of gravity of the human body and decides that the human body is falling or in a transition toward falling when the displacement is outside the predetermined area.

17. An equilibrium state analysis method comprising, an acceleration information detecting step of detecting at least one linear acceleration within the horizontal plane by acceleration information detecting means mounted to a trunk of a body, a motion information storing step of storing the detected acceleration and an equilibrium state analyzing step of analyzing the equilibrium state of the human body by integrating the stored acceleration information, wherein the acceleration information detecting step includes time sampling, in a measuring period, the detected linear acceleration and the equilibrium state analyzing step includes calculating and outputting an average velocity over the measuring period by integrating the time-sampled acceleration.

* * * * *

UNITED STATES PATENT AND TRADEMARK OFFICE
CERTIFICATE OF CORRECTION

PATENT NO. : 7,031,872 B2
APPLICATION NO. : 10/497327
DATED : April 18, 2006
INVENTOR(S) : Tanaka et al.

It is certified that error appears in the above-identified patent and that said Letters Patent is hereby corrected as shown below:

On the cover page, item (54) please replace the Title because of a spelling error:

--EQUILIBRIUM STATE ANALYZING APPARATUS, EQUILIBRIUM STATE ANALYSIS METHOD, PROGRAM AND RECORDING MEDIUM--

At Column 18, line 14, "accelerations generated within" should read --acceleration generated within--

At Column 20, line 10, "plane; motion information storing means of storing said detected accelerations; and" should read -- plane;

motion information storing means of storing said detected accelerations; and--

Signed and Sealed this

Tenth Day of October, 2006

JON W. DUDAS
*Director of the United States Patent and Trademark Office*